United States Patent
Hovland et al.

[19]

[11] Patent Number: 6,149,667
[45] Date of Patent: Nov. 21, 2000

[54] DEVICES AND METHODS FOR TREATING E.G. URINARY STRESS INCONTINENCE

[75] Inventors: Claire T. Hovland, Minnetonka; Jerome H. Abrams, St. Paul, both of Minn.

[73] Assignee: Surgical Connections, Inc., Bloomington, Minn.

[21] Appl. No.: 09/309,617

[22] Filed: May 11, 1999

Related U.S. Application Data

[60] Provisional application No. 60/085,054, May 11, 1998.

[51] Int. Cl.$^7$ ............................... A61B 17/04; A61F 2/00
[52] U.S. Cl. .................... 606/219; 600/29; 128/DIG. 25; 227/19; 227/175.1; 227/179.1
[58] Field of Search .................................. 606/153, 152, 606/219; 227/19, 175.1, 179.1; 128/89, DIG. 25; 600/29, 30

[56] References Cited

U.S. PATENT DOCUMENTS

| | | | |
|---|---|---|---|
| 2,638,901 | 5/1953 | Sugarbaker | 606/153 |
| 3,661,155 | 5/1972 | Lindan . | |
| 4,019,499 | 4/1977 | Fitzgerald . | |
| 4,139,006 | 2/1979 | Corey . | |
| 4,294,255 | 10/1981 | Geroc | 606/153 |
| 4,686,962 | 8/1987 | Haber . | |
| 5,007,894 | 4/1991 | Enhorning | 600/29 |
| 5,222,963 | 6/1993 | Brinkerhoff et al. | 606/153 |
| 5,234,409 | 8/1993 | Goldberg et al. | 604/96 |
| 5,250,058 | 10/1993 | Miller et al. | 606/153 |
| 5,256,133 | 10/1993 | Spitz | 600/29 |
| 5,417,226 | 5/1995 | Juma | 128/885 |
| 5,520,606 | 5/1996 | Schoolman et al. | 600/31 |
| 5,611,515 | 3/1997 | Benderev et al. | 128/898 |
| 5,647,836 | 7/1997 | Blake, III et al. | 600/30 |

FOREIGN PATENT DOCUMENTS

| | | |
|---|---|---|
| 0517488 | 12/1992 | European Pat. Off. . |
| 2612392 | 9/1988 | France . |
| 9107166 U | 9/1991 | Germany . |
| 7400096 | 7/1975 | Netherlands . |
| 9803118 | 1/1998 | WIPO . |

OTHER PUBLICATIONS

ACOG Patient Education brochure "Cynecologic Problems: Urinary Incontinence", The American College of Obstetricians and Gynecologists, Jan. 1996.

"Urethral Sphincter Incompetence (Stress Incontinence)", by S.L. Stanton, Urodynamics Principles, Practice and Application, Chapter 22, 1984, pp. 229–241.

"The Scott Artificial Urinary Sphincter", Urodynamics Principles, Practice and Application, Chapter 35, 1984, pp. 374–377.

"Urinary Incontinence in the Female: Stress Incontinence", by Linda Shortliffe, M.D. et al., Campbell's Urology, Fifth Edition, vol. 3, Chapter 73, 1986, pp. 2680–2711.

*Primary Examiner*—Gary Jackson
*Attorney, Agent, or Firm*—Paterson, Thuente & Skaar, P.A.

[57] ABSTRACT

Embodiment of the invention provide a permanent implanted support for e.g. the urethral neck of the bladder, substantially preventing urinary leakage caused by transmission of intra-abdominal pressure pulse waves. The support is implanted in a straightforward manner without the significant complexity and invasiveness associated with known surgical techniques. Pelvic trauma is dramatically reduced. Embodiments of the invention can be used in treament of stress incontinence, and other types of incontinence, in both males and females.

35 Claims, 24 Drawing Sheets

NORMAL    DESCENT    WIDE AND SHORT URETHRA

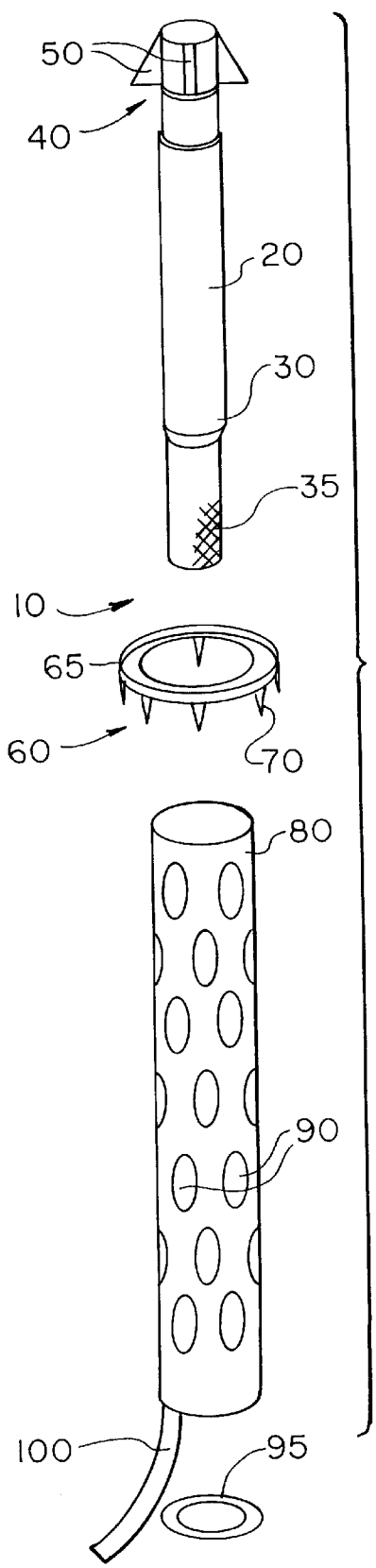
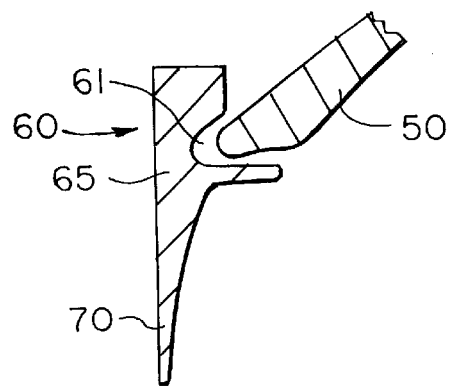
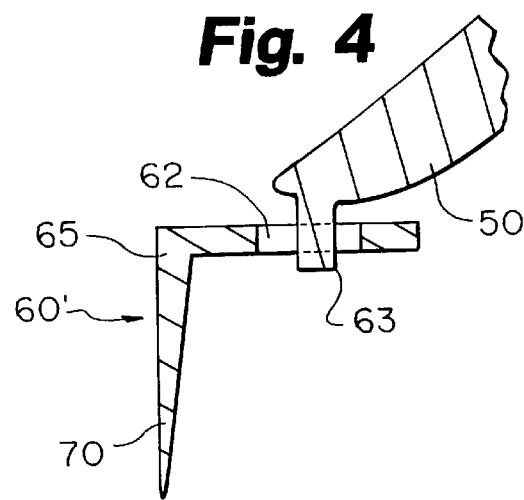
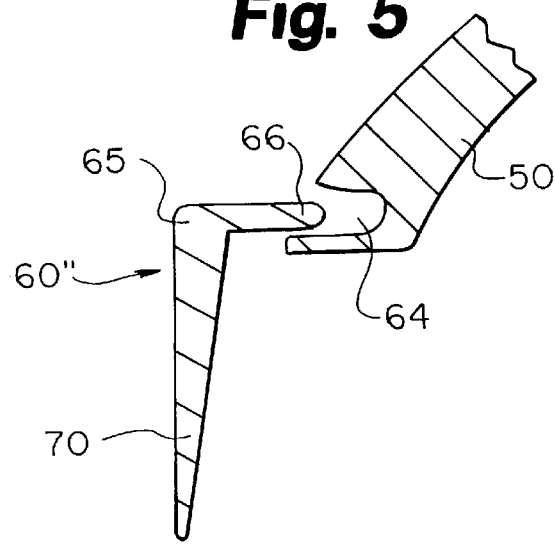

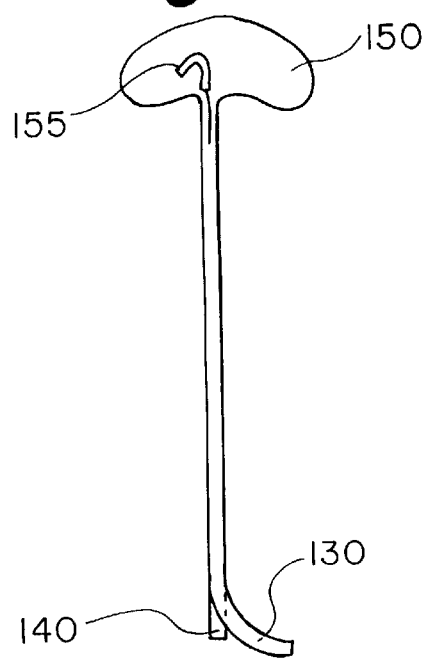
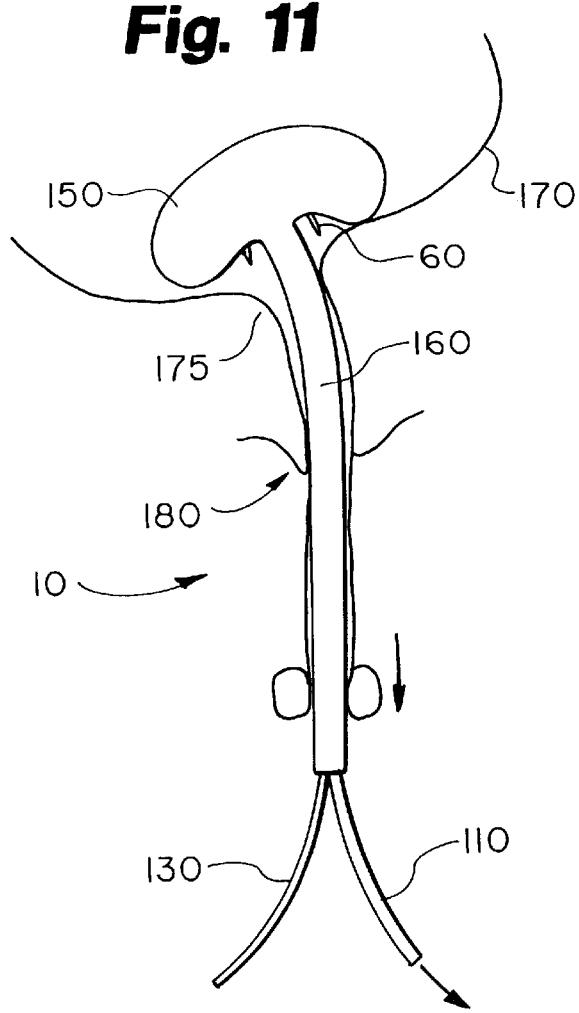
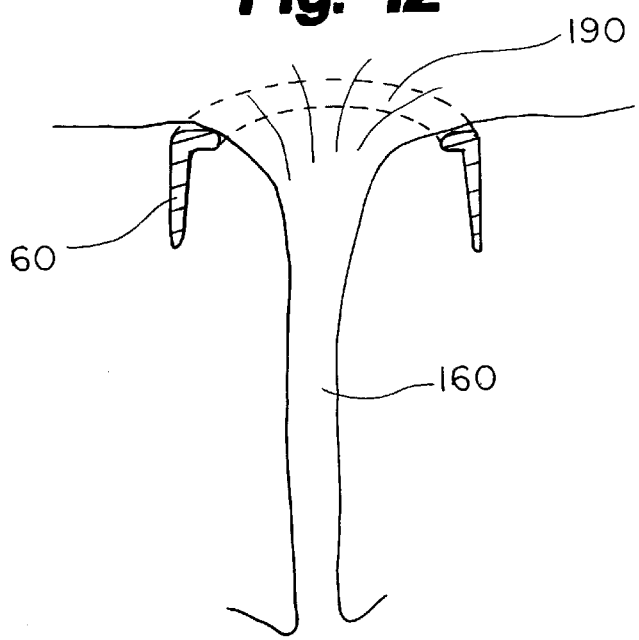

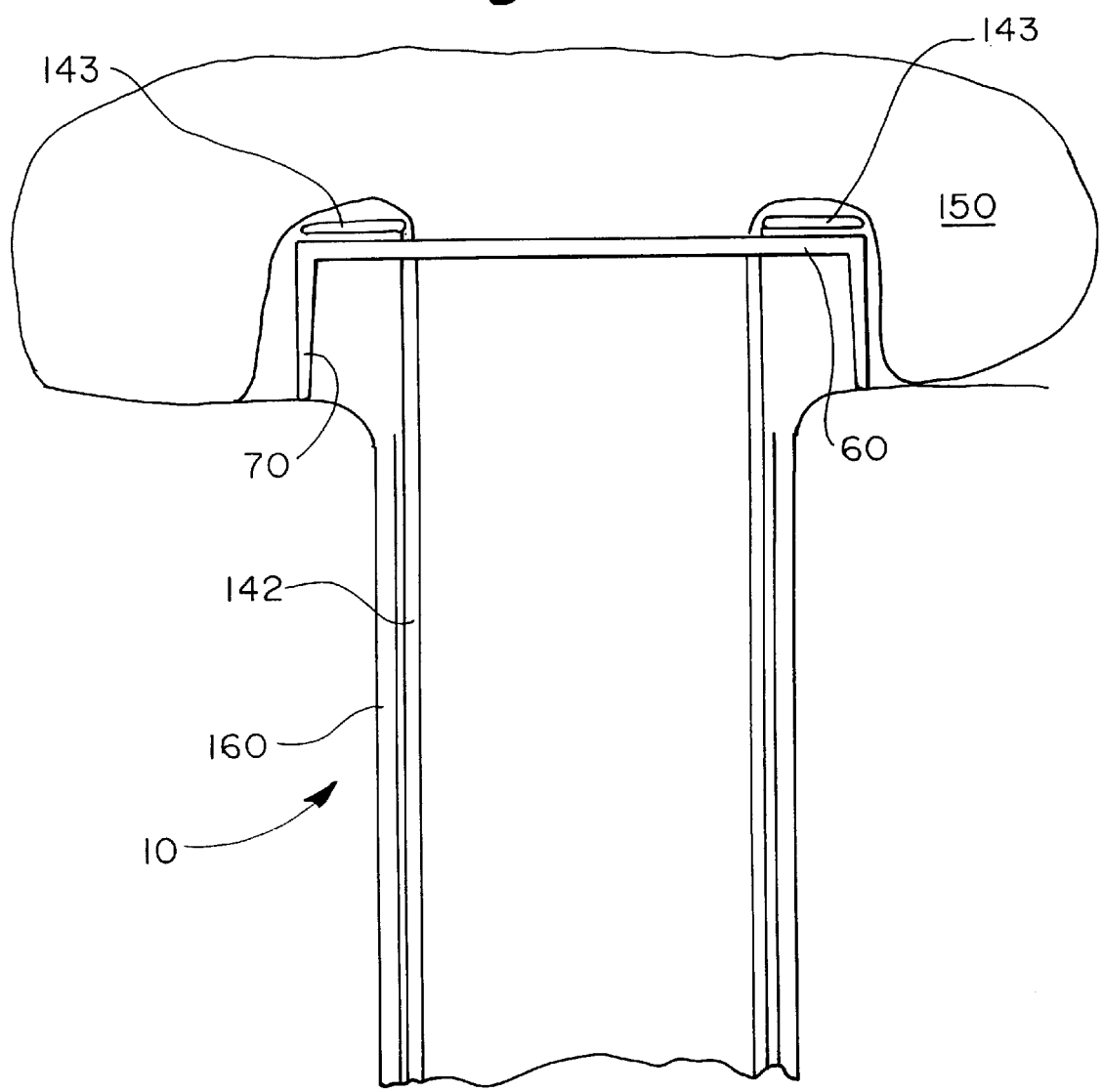

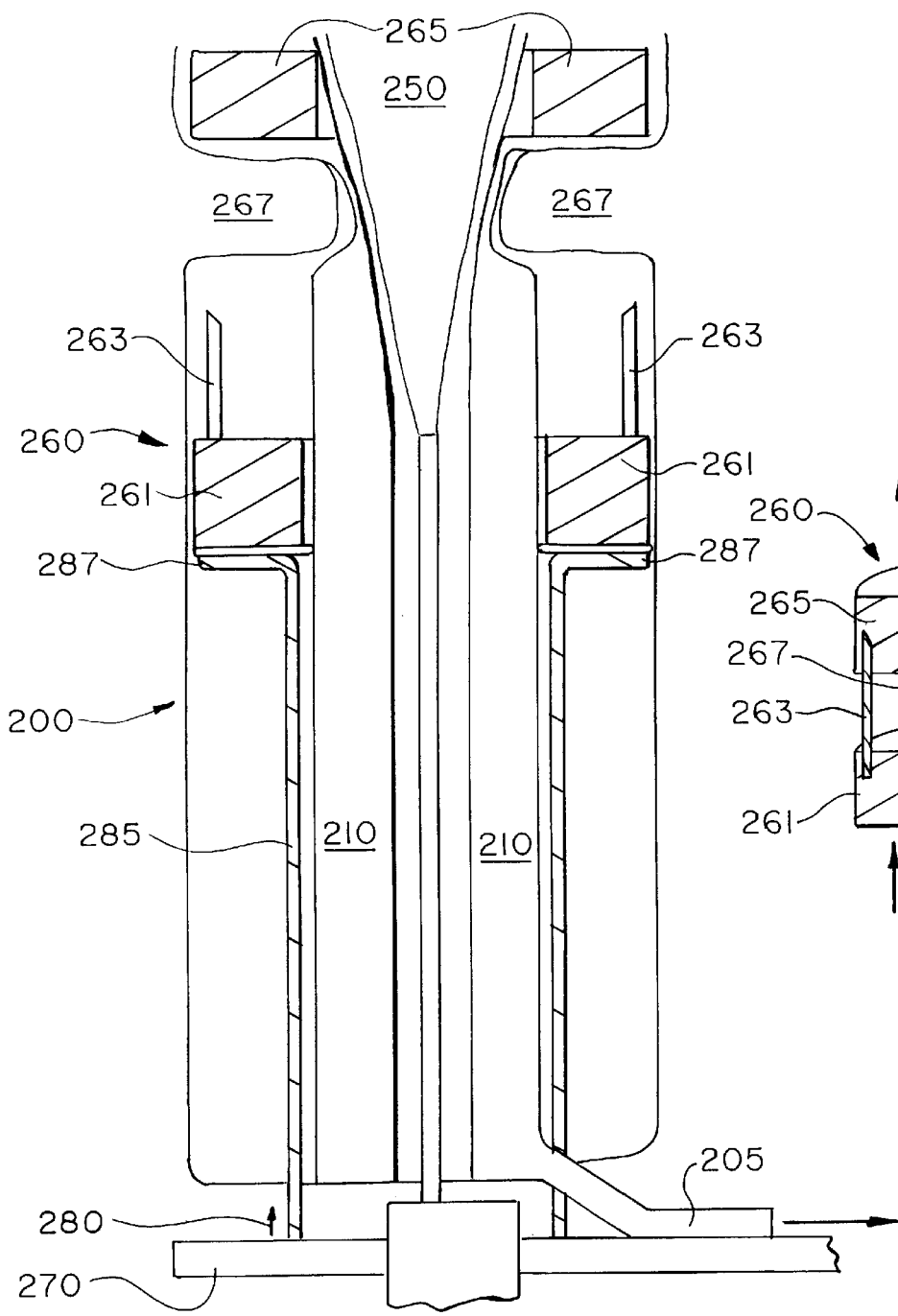

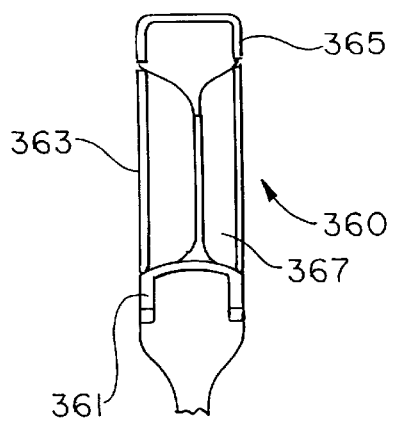
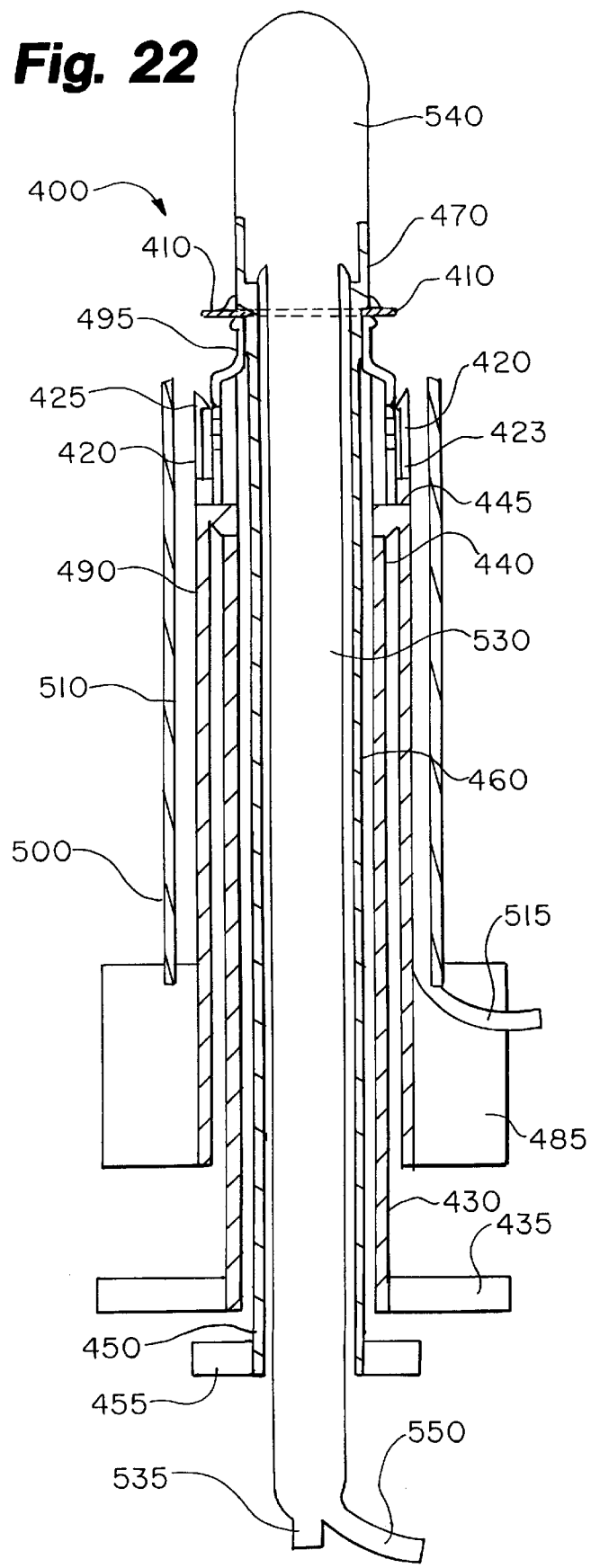

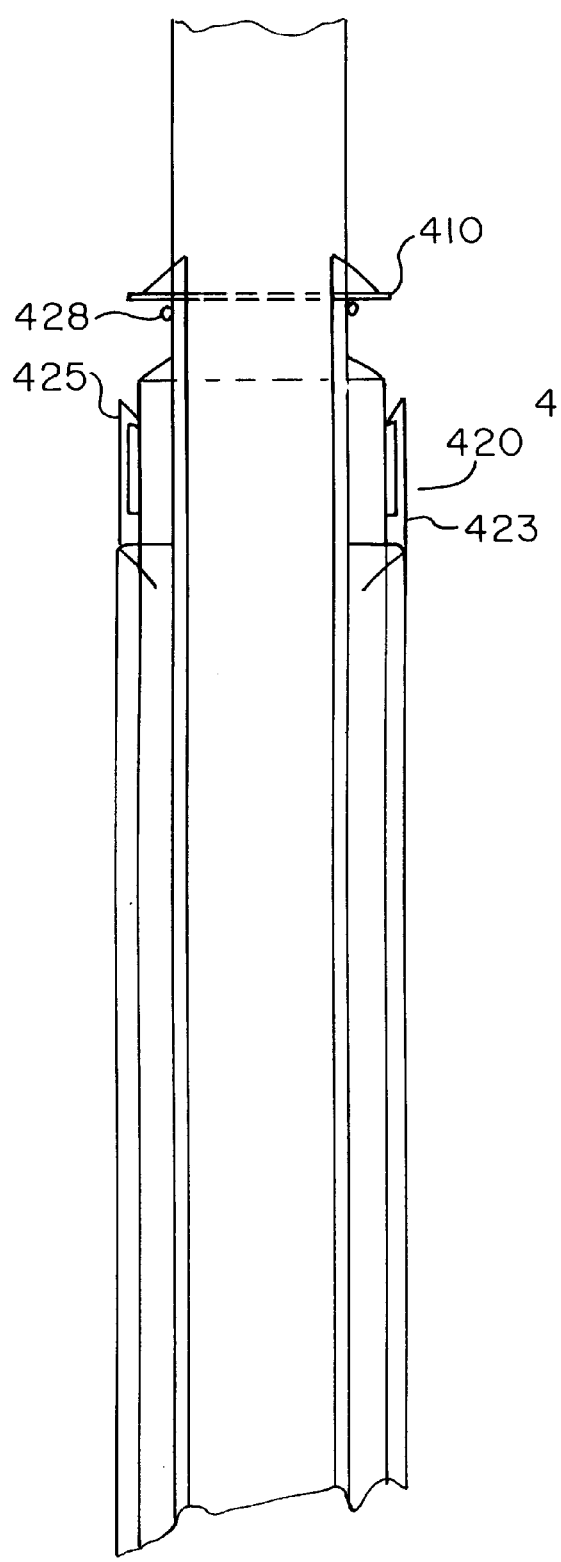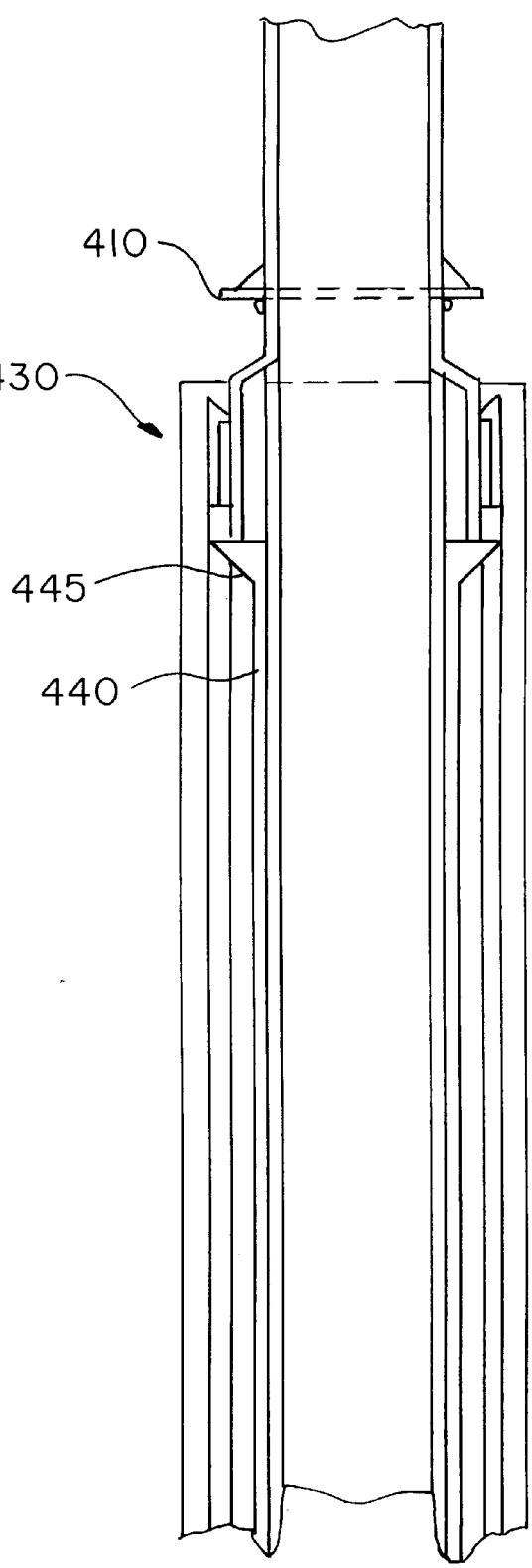

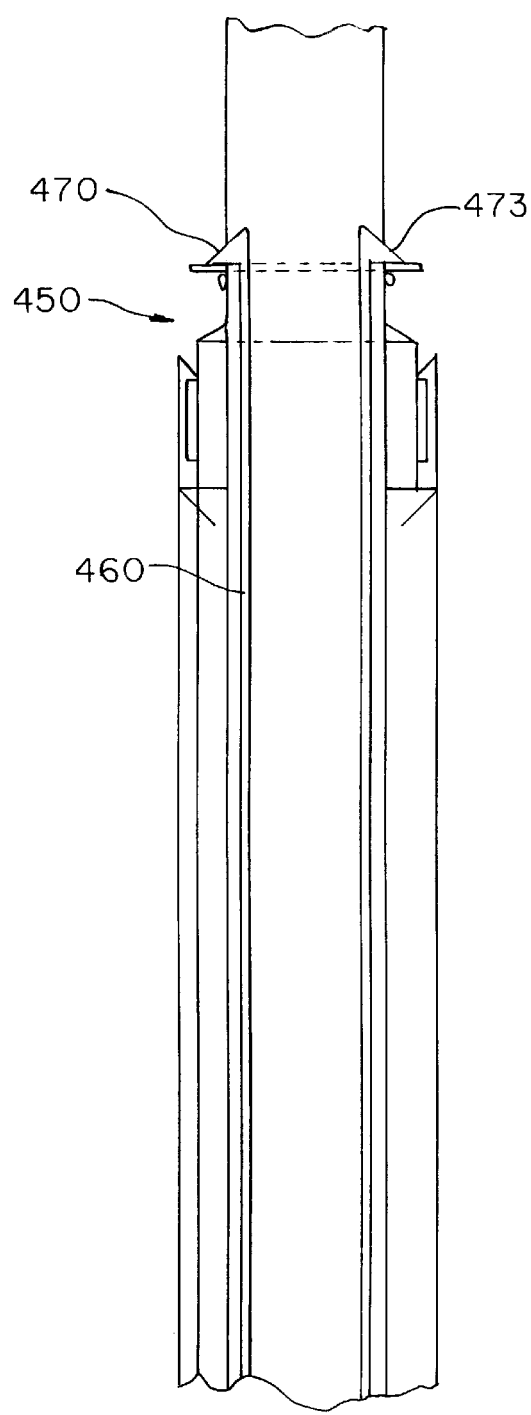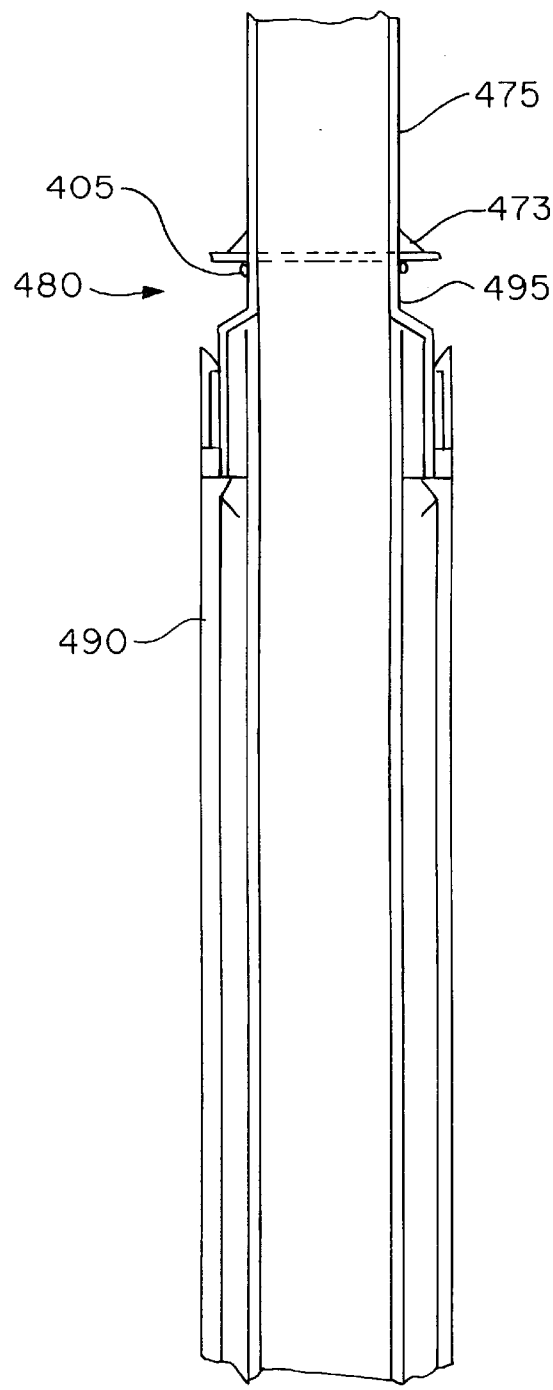

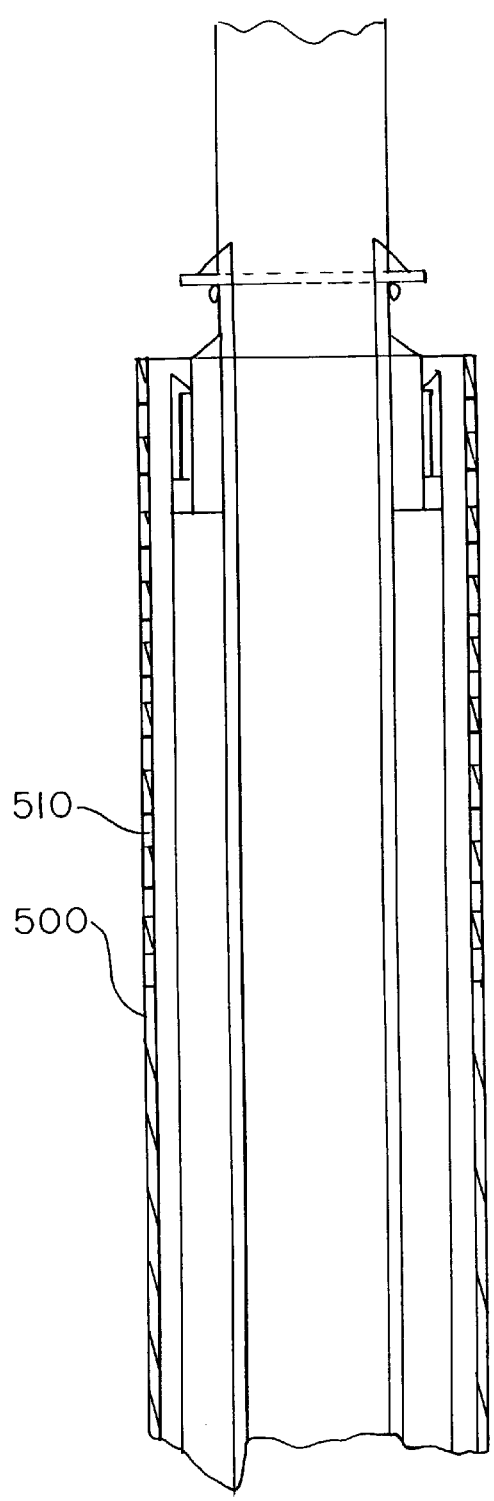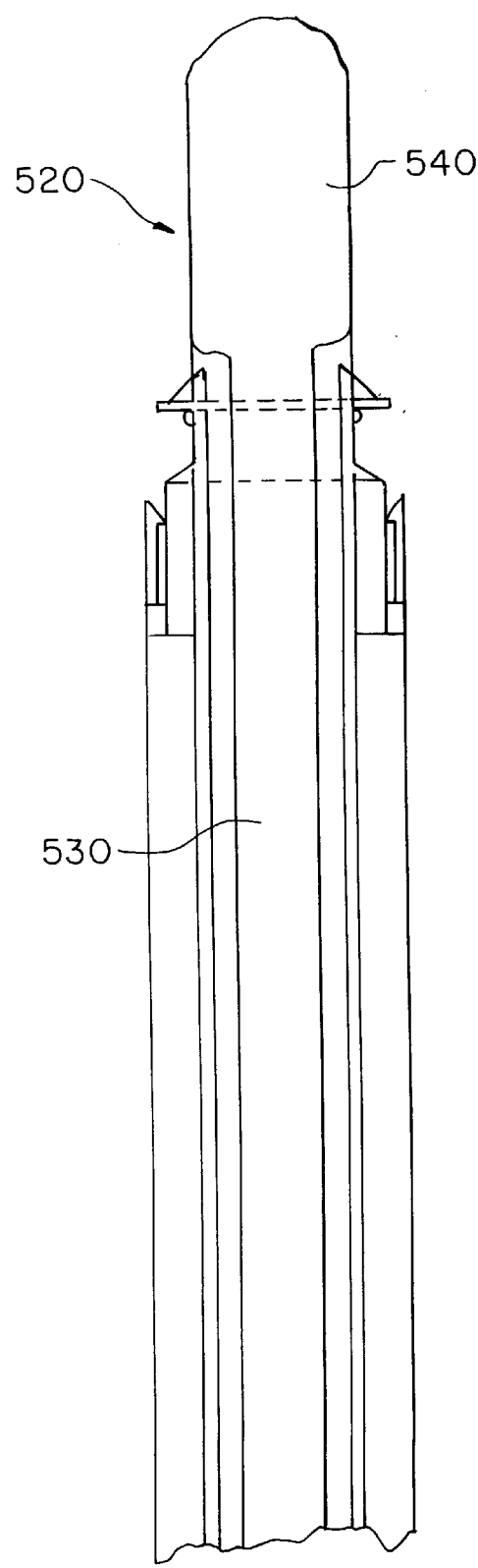

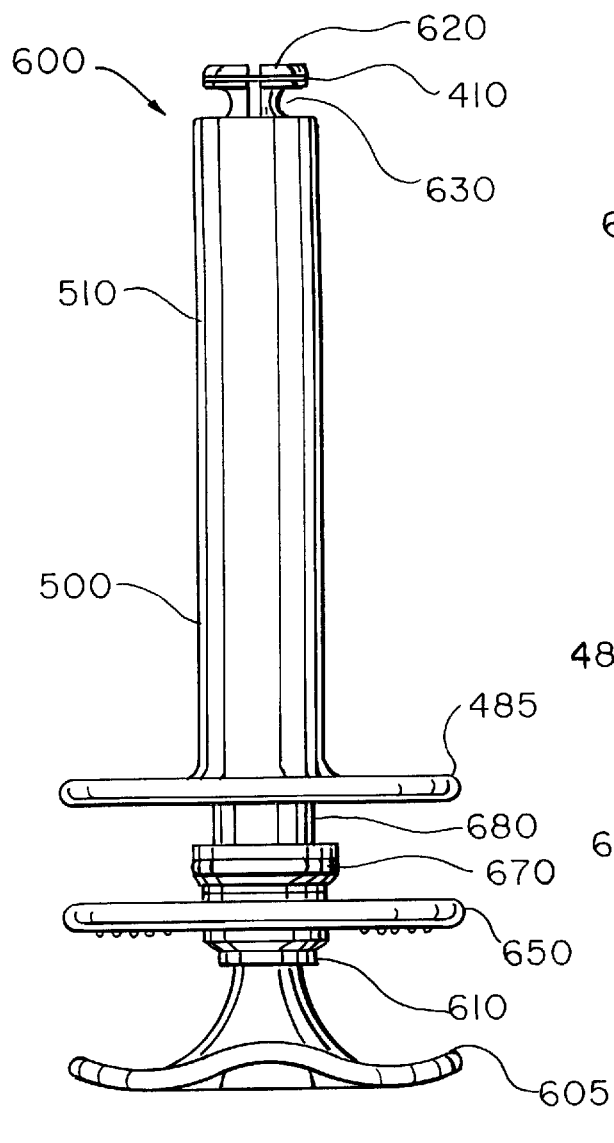
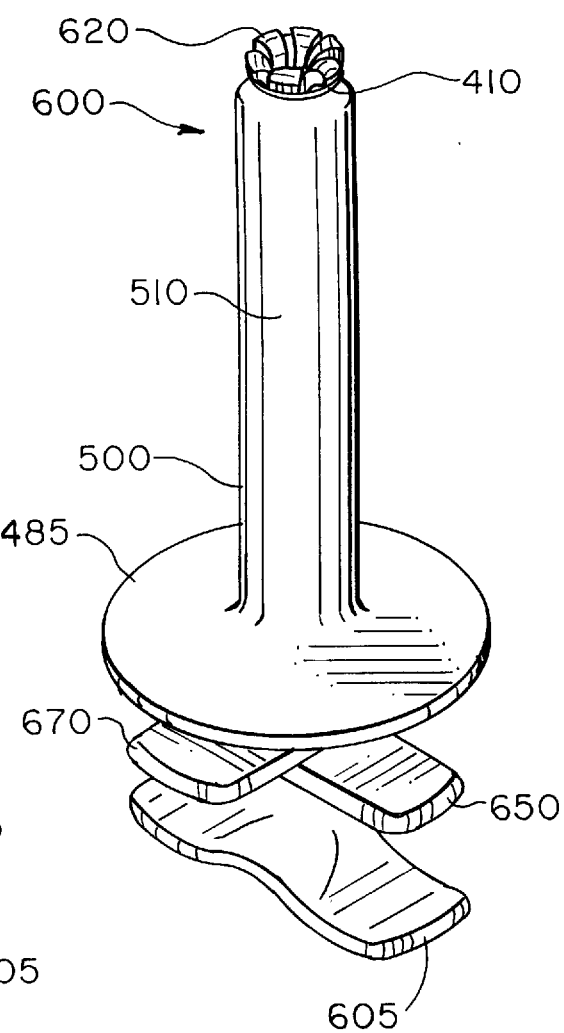

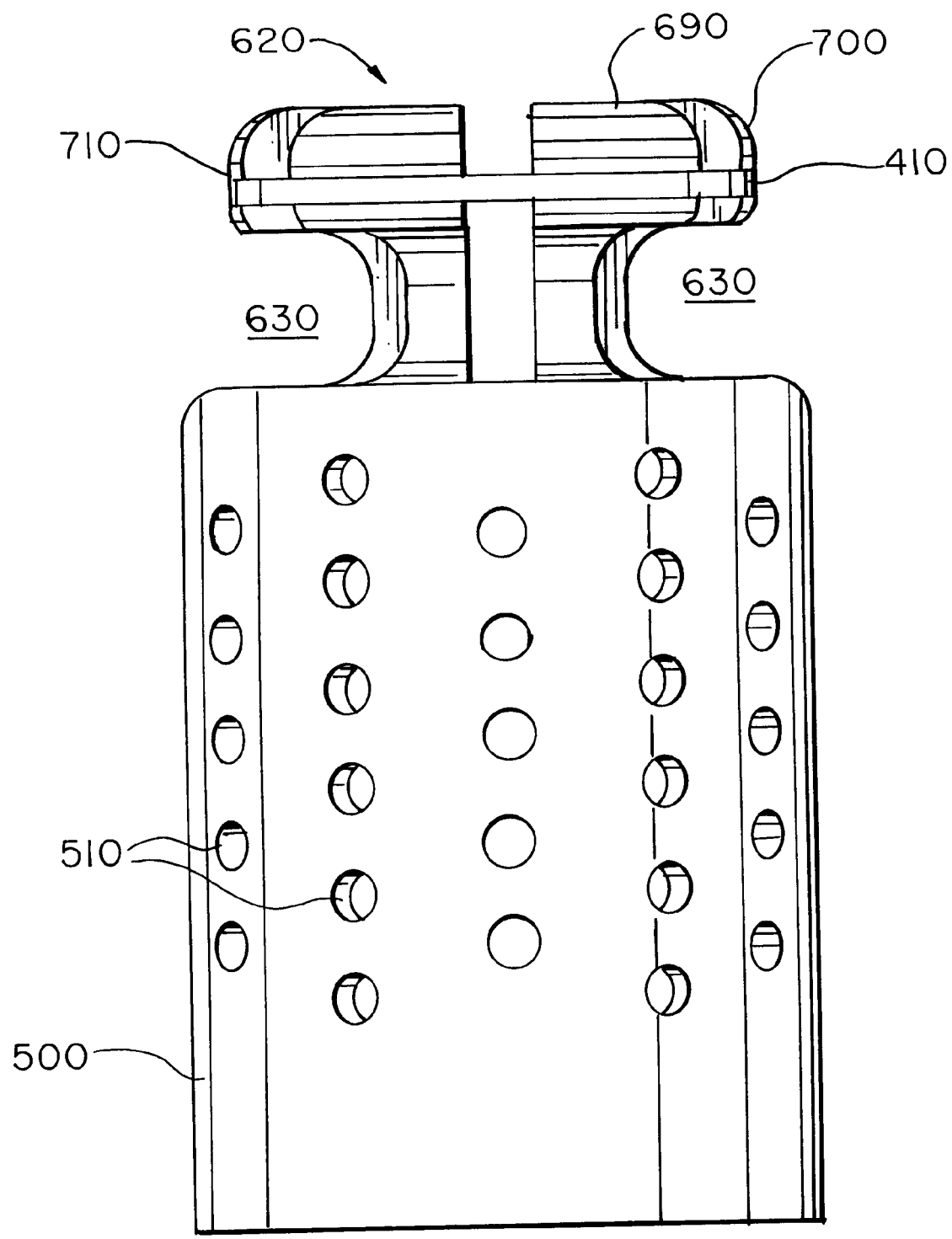

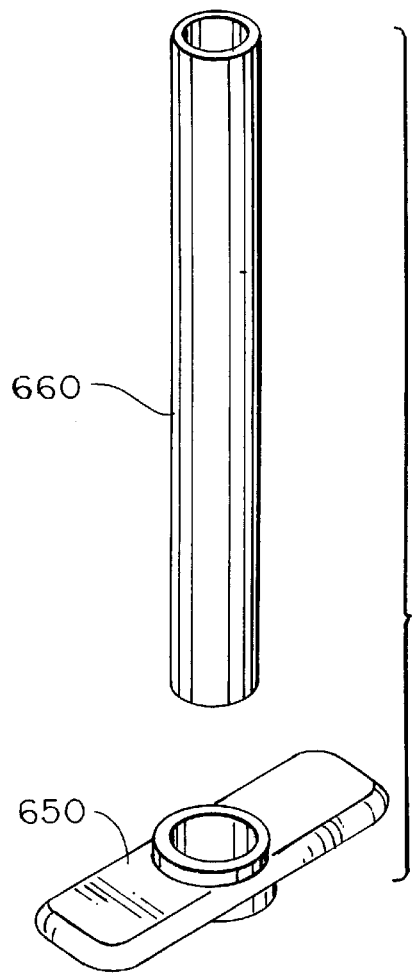
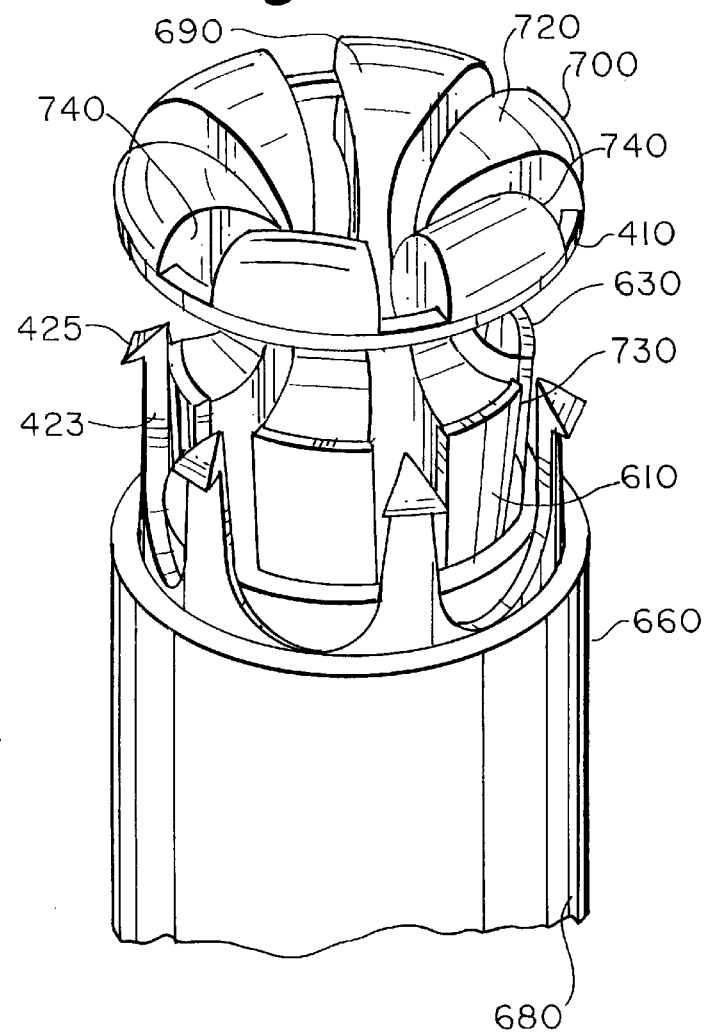

DEVICES AND METHODS FOR TREATING E.G. URINARY STRESS INCONTINENCE

CROSS-REFERENCE TO RELATED APPLICATION

The subject matter of this application is related to the subject matter of U.S. Provisional Patent Application No. 60/085,054, filed May 11, 1998, priority to which is claimed under 35 U.S.C. §119(e) and which is incorporated in its entirety herein by reference.

BACKGROUND OF THE INVENTION

1. Field of the Invention

The invention relates to devices and methods for treating urinary incontinence. More specifically, the invention relates to surgical devices and methods for eliminating or reducing urinary stress incontinence, particularly (though not exclusively) in minimally invasive surgical settings.

2. Description of Related Art

Urinary incontinence involves the involuntary passage of urine. A wide range of disorders and conditions can cause urinary incontinence, including injuries to the pelvic region, pregnancy/childbirth, infection, and degenerative changes associated with aging. In a healthy patient, on the other hand, urine remains in the bladder until the patient voluntarily causes it to flow through the urethra and out of the body.

Currently, an estimated 13 million Americans suffer some form of incontinence. As many as 85% of them are women, and indeed it is believed that as many as one in four women aged 30–59 has experienced at least one episode of urinary incontinence. Naturally, incontinence causes not only physical discomfort and inconvenience but also has emotional and psychological consequences as well.

Five forms of incontinence are generally recognized. Stress incontinence, an important focus of the present invention, often occurs when the pelvic muscles have deteriorated or been damaged. Coughing, sneezing, laughing, and other activities that put pressure on the abdomen and bladder may cause leakage. Stress incontinence is discussed further below. With another type of incontinence, known as urge incontinence, nerve passages between the bladder and brain are damaged. This damage causes sudden, seemingly uncontrollable bladder contractions that then cause leakage of urine. With overflow incontinence, the bladder's capacity is exceeded by the quantity of urine produced. Reflex incontinence, in which the patient generally is unaware of the need to urinate, can result from a leak in the bladder, urethra, or ureter, or an abnormal opening in the bladder. Finally, incontinence can be caused by certain surgical procedures involving e.g. the urethra or bladder neck. A single patient can have multiple forms of incontinence.

Stress incontinence often is caused by weakened muscles in the pelvic floor, as referenced earlier. Without adequate pelvic support, the bladder and proximal end of the urethra tend to sag, the bladder neck dilates, the proximal urethra widens, and the urethra as a whole shortens. Normal flow resistance from the bladder neck and the urethral sphincter decreases, causing leakage upon increase in intra-abdominal pressure that might be due to coughing, for example. FIG. 1 roughly illustrates three anatomical configurations with respect to pelvic floor 2: normal anatomy 4, descended bladder/urethra 6, and widened bladder neck/shortened urethra 8. FIG. 1 is adapted from Mundy, A. R., ed., Urodynamics—Principles, Practice and Application, 1984, p. 229. The Urodynamics text is incorporated by reference herein in its entirety.

Recent research suggests that incontinence requires multiple anatomic defects, not just one, and that the mere position of the urethra does not predict urinary incontinence. At least four anatomic factors are believed involved, namely, urethral length; support of the bladder neck and urethra by the pubo-urethral, urethropelvic, vesicopelvic and cardinal ligaments; changes in the bladder neck and urethra during times of stress; and coaptation of the urethra. The two most important factors in female urinary incontinence, recent research suggests, are hypermobility of the bladder neck and defective support of the midurethra. Note the discussion of this topic in "Anatomy of female continence redefined by photographs, imaging techniques," Urology Times of Canada, April, 1996, which is incorporated herein by reference.

Many varieties of general surgical procedures are used to treat stress incontinence. Most, if not all, such procedures involve open/endoscopic surgery and are significantly invasive, requiring general anesthesia and hospitalization. Such procedures are peri-urethral, i.e. they are performed from outside the urethra. Suspension procedures, for example, use sutures to lift the urethra and bladder neck to their normal positions. Sling procedures use synthetic material or tissue, often anchored to bone, to do the same. In some cases, an implantable artificial sphincter is used to restore the compressive action needed to stop the flow of urine.

Various invasive surgical procedures are described in the Urodynamics text referenced above. Additional discussion is found in Campbell's Urology, 5th ed., 1986, which is incorporated by reference herein. Additional methods and devices for treatment of incontinence are disclosed in, among others, U.S. Pat. Nos. 5,647,836, 5,611,515, 5,520,606, 5,417,226, 5,256,133, 5,234,409, 5,007,894, 4,857,041, 4,686,962, 4,139,006, 4,019,499, and 3,661,155, all of which are incorporated herein by reference.

As referenced above, most, if not all, known surgical procedures and devices for treating stress incontinence successfully are significantly invasive, complicated, or both. Significant trauma to the pelvic region can result. Additionally, although stress incontinence primarily affects females and thus the majority of known surgical procedures are directed at female patients, a significant number of males suffer stress incontinence as well. A need has arisen, therefore, to treat both female and male stress incontinence with minimal complexity and minimal invasiveness. Embodiments of the invention address complexity, invasiveness, and other problems.

SUMMARY OF THE INVENTION

Embodiments of the invention provide a permanent implanted support for e.g. the urethral neck of the bladder, substantially preventing urinary leakage caused by transmission of intra-abdominal pressure pulse waves. The support is implanted in a straightforward manner without the significant complexity and invasiveness associated with known surgical techniques. Pelvic trauma is dramatically reduced. Embodiments of the invention can be used in treatment of stress incontinence, and other types of incontinence, in both males and females.

More specifically, according to one embodiment, a surgical staple device comprises a substantially ring-shaped hollow base portion, a plurality of needle members upstanding from the base portion, and a substantially ring-shaped locking member for receiving the needle members. The locking member initially is separated from the base portion and needle members. The locking member has an inside portion and an outside portion, the inside portion of the locking member being constructed to receive the needle members and the needle members being constructed to enter into locking engagement with respect to the locking member. The surgical staple device is constructed of a biocompatible material.

The needle members are substantially flexible with respect to the base portion, tand snap into locking engagement with the locking member. The needle members each include a tapered upper surface for engaging the inner surface of the locking member and for sliding with respect to the inner surface of the locking member as the needle members are advanced into the locking member. The needle members each snap into place with respect to the locking member, once the tapered upper surface clears the inside portion of the locking member.

The base portion defines a plurality of detents for supporting the base portion with respect to a staple insertion mechanism. The detents are disposed directly underneath the upstanding needle members on a side of the base portion opposite the needle members. The base portion is substantially circular.

According to another aspect of the invention, a surgical treatment device includes a surgical staple, the surgical staple comprising a substantially ring-shaped hollow base portion, a plurality of needle members upstanding from the base portion, and a substantially ring-shaped locking member for receiving the needle members, the locking member initially being separated from the base portion and needle members, the locking member having an inside portion and an outside portion, the inside portion of the locking member being constructed to receive the needle members and the needle members being constructed to enter into locking engagement with respect to the locking member, wherein the surgical staple device is constructed of a biocompatible material. The surgical treatment device further includes delivery structure for supporting the surgical staple and delivering the surgical staple to a desired anatomical site of a patient, movement apparatus, operatively coupled with the delivery structure, for moving anatomical tissue into position between the needle members and the locking member, and a staple advancing mechanism for advancing the needle members through the anatomical tissue and into locking engagement with the locking member, the surgical staple thus holding the anatomical tissue in a desired configuration.

The movement apparatus comprises a vacuum device for drawing desired tissue into a new anatomical position. The movement apparatus further comprises a blocking device, operatively coupled with the vacuum device, for preventing the vacuum device from applying vacuum to a portion of the anatomy of the patient. The blocking device comprises an inflatable mechanism, and the movement apparatus is physically connected to the delivery structure. The surgical treatment device is constructed for use in minimally invasive surgical procedures.

According to another aspect of the invention, a surgical treatment device, comprises delivery structure for supporting a surgical staple and delivering the surgical staple to a desired anatomical site of a patient, movement apparatus, operatively coupled with the delivery structure, for moving anatomical tissue into position with respect to the surgical staple, the movement apparatus comprising a vacuum device, and a staple advancing mechanism for moving the surgical staple into a locked configuration with respect to the anatomical tissue, the surgical staple thus holding the anatomical tissue in a desired configuration.

The movement apparatus further comprises a blocking device, operatively coupled with the vacuum device, for preventing the vacuum device from applying vacuum to a portion of the anatomy of the patient. The blocking device comprises an inflatable mechanism. The blocking device further comprises a balloon constructed for insertion into the bladder of the patient, further wherein the anatomical tissue is at least a portion of the bladder neck and/or urethra.

The delivery structure comprises a staple retaining mechanism, the staple retaining mechanism comprising a plurality of sprung leg members. The staple retaining mechanism further comprises a groove for accommodating a locking ring of the surgical staple. The sprung leg members define a plurality of gaps therebetween, the gaps accommodating upstanding portions of the surgical staple.

The delivery structure comprises a plurality of concentrically disposed substantially cylindrical members, one of the substantially cylindrical members being constructed to advance the staple into the locked configuration, and another of the substantially cylindrical members being constructed to release the staple from the delivery structure after the locked configuration has been achieved. The delivery structure also comprises a plurality of handles for actuation by a user of the device, one of the handles being constructed to advance the staple into the locked configuration, and another of the substantially cylindrical members being constructed to release the staple from the delivery structure after the locked configuration has been achieved.

The delivery structure further comprises locking structure for substantially fixing the angular position of the handles with respect to each other. The locking structure comprises at least one locking rod extending through or alongside the handles.

The vacuum device comprises a substantially cylindrical member defining vacuum apertures. The vacuum device is substantially concentrically disposed with respect to the delivery device.

According to another aspect of the invention, a method of treating urinary incontinence in a patient comprises inserting a surgical treatment device into at least the urethra of the patient, applying a vacuum with the surgical treatment device to draw at least a urethra portion and/or a bladder neck portion of the patient into a desired configuration, delivering a surgical staple to the patient with the device, the staple holding the desired configuration, releasing the staple from the device, and withdrawing the device from the patient.

The method also comprises, according to one embodiment, inserting a balloon into the bladder of the patient, inflating the balloon, blocking application of vacuum to at least the bladder with the balloon, deflating the balloon, and withdrawing the balloon from the patient.

According to another aspect of the invention, urinary incontinence treatment apparatus comprises means for applying a vacuum to draw at least a urethra portion and/or bladder neck portion of a patient into a desired configuration, means for delivering a surgical staple to the patient, the staple holding the desired configuration, and means for releasing the staple so that it remains within the patient. The apparatus further comprises means for blocking application of vacuum to at least the bladder, and means for withdrawing the means for blocking from the patient. The means for blocking comprises a balloon.

Other embodiments and aspects of the invention will be apparent from the following detailed description.

BRIEF DESCRIPTION OF THE DRAWINGS

Embodiments of the invention will be described with reference to the figures, in which like reference numerals denote like elements and in which:

FIG. 2 is an exploded perspective view of an incontinence treatment device according to an embodiment of the invention;

FIGS. 3–6 are cross-sectional views showing supportive interaction with a staple, according to embodiments of the invention;

FIG. 10 shows a balloon and endoscope port according to an embodiment of the invention;

FIG. 11 shows an incontinence treatment device inserted into the urethra and bladder, according to an embodiment of the invention;

FIG. 12 shows an implanted staple with healed-over tissue, according to an embodiment of the invention;

FIG. 13 shows a more detailed view of an inserted incontinence treatment device according to an embodiment of the invention;

FIG. 14 shows an incontinence treatment device according to an alternative embodiment of the invention;

FIG. 15 is a detail view of the device shown in FIG. 14;

FIG. 21 shows an alternative staple, according to an embodiment of the invention;

FIG. 22 is a cross-sectional view of an incontinence treatment device according to an alternative embodiment;

FIG. 23 is a cross-sectional view of a staple ring and a staple mounted on an insertion device, according to an embodiment of the invention;

FIG. 24 is a cross-sectional view of a staple insertion/actuator mechanism, according to an embodiment of the invention;

FIG. 25 shows a staple ring retainer/release mechanism according to an embodiment of the invention;

FIG. 26 shows a mounting device, according to an embodiment of the invention;

FIG. 27 shows a vacuum retainer mechanism, according to an embodiment of the invention;

FIG. 28 shows a balloon and catheter assembly, according to an embodiment of the invention;

FIG. 29 is a side view of an incontinence treatment device according to an alternative embodiment of the invention;

FIG. 30 is a perspective view of the FIG. 29 device;

FIG. 32 is a side view of an upper portion of the FIG. 29 device;

FIG. 36 is a partial exploded view of a staple insertion/actuator mechanism, according to an embodiment of the invention;

FIG. 37 is a perspective view showing an incontinence treatment device with relatively extended staple-ring engaging tips, according to an embodiment of the invention;

DETAILED DESCRIPTION OF PREFERRED EMBODIMENTS

Figure 1:
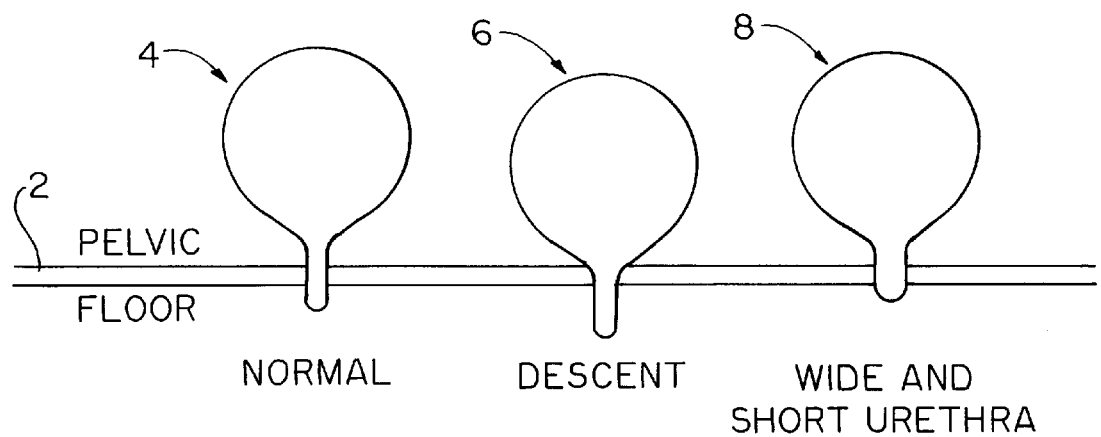
FIG. 1 illustrates three anatomical configurations of the bladder and urethra.

Embodiments of the invention relate to devices and methods for treating incontinence, primarily urinary stress incontinence (USI). Although many if not most known surgical procedures and devices for treating USI are intended for the female population, embodiments of the invention are applicable equally to both females and males. Therefore, references in this application to female anatomy or treatment should be interpreted as applying equally to males, as well. Further, although embodiments of the invention are particularly well-suited for minimally invasive surgery, conventional surgical techniques also can be used, and this application should be interpreted accordingly. Other types of incontinence, e.g. surgically induced incontinence, also can be treated in certain circumstances. As will become clear, embodiments of the invention treat USI in a relatively uncomplicated, minimally invasive, and cost-effective manner not believed known or contemplated by the prior art.

FIG. 2 shows an exploded view of incontinence treatment device 10 according to an embodiment of the invention. Device 10 includes staple holder 20, having elongated shaft 30 terminating in handle 35. At the end of shaft 30 opposite handle 35 is staple mount 40 with retractable, tapered support portions or wings 50. Staple 60, having an annulus 65 with descending teeth or needles 70 as will be described, is secured to staple mount 40 during initial placement of device 10. Staple 60, as with all the staples described and/or illustrated in this application, preferably is formed of a biocompatible material.

According to embodiments of the invention, the outermost portions of retractable wings 50 each include a protrusion, such as a pin, extending therefrom. FIGS. 3–4 illustrate two of these embodiments. In FIG. 3, staple 60 is provided with a substantially U-shaped groove 61 extending around the interior circumference of annulus 65. Of course, substantially V-shaped or other-shaped grooves are also contemplated, as is a groove extending around the exterior circumference of annulus 65. Multiple grooves in a single staple are also contemplated, with correspondingly shaped engaging wing structure. In FIG. 4, staple 60' is provided with a plurality of downwardly directed holes 62 through annulus 65, for example, through which corresponding downwardly directed pins 63 extend. Radially extending pins and holes are also contemplated. When wings 50 are in an extended position, the ends or pins of the wings engage the groove or holes of annulus 65 to secure staple 60 on staple mount 40. Other mating configurations are contemplated as well. In FIG. 5, for example, each wing 50 has groove 64 extending therethrough to accommodate corresponding portions 66 of staple 60", which portions can be raised or ridged.

Figure 6:
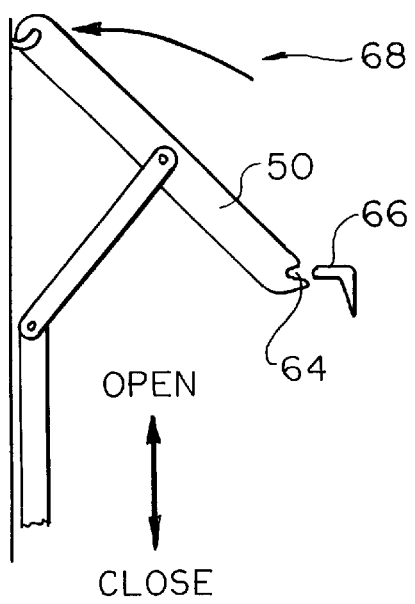

Wings 50 preferably are spring-biased to an extended position, according to embodiments of the invention, for engaging and holding staple 60. Wings 50 can be retracted by a screw mechanism, extending through staple holder 20 and emerging near handle 35 for manipulation by the surgeon. Alternatively, wings 40 can be extended and retracted by telescoping and clasping mechanism 68, similar to that found on conventional umbrellas, as shown, for example, in FIG. 6. Although FIG. 6 shows the mating configuration of FIG. 5, use with alternative mating configurations is also contemplated.

Returning to FIG. 2, device 10 also includes vacuum support 80, having a plurality of vacuum apertures 90. Vacuum support 80 is substantially hollow and is constructed to receive and accommodate staple holder 20. At the lower end of vacuum support 80, O-ring vacuum seal 95 provides a fluid-tight seal and allows handle 35 of holder 20 to extend therethrough. Vacuum port 100 is provided to draw a vacuum through support 80 and vacuum apertures 90.

Figure 7:
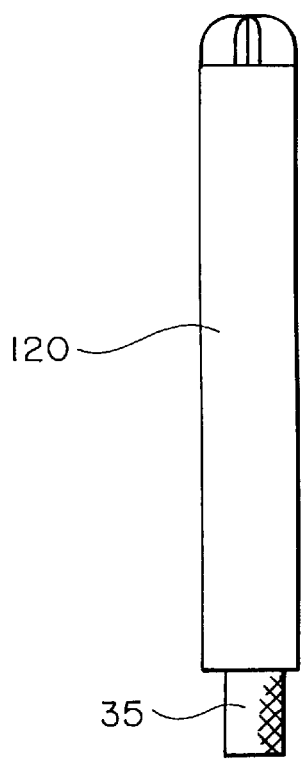
FIG. 7 shows an incontinence treatment device in a substantially assembled condition, according to an embodiment of the invention.
Figure 8:
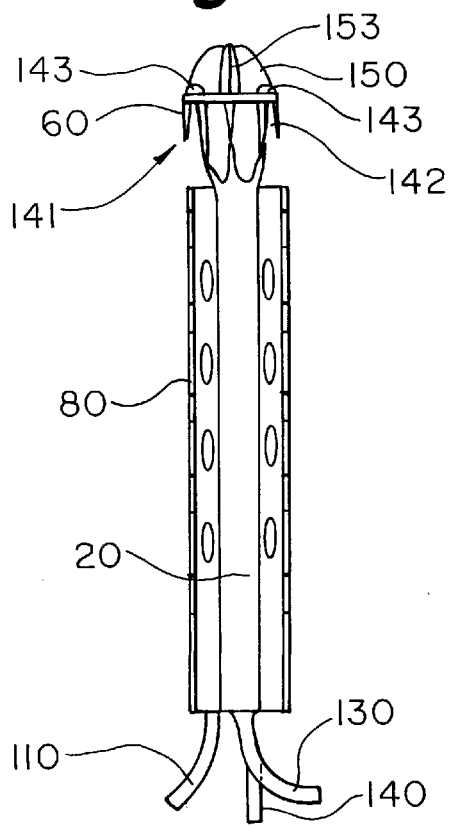
FIG. 8 shows the incontinence treatment device of FIG. 7 with the cover removed.

FIGS. 7–8 show device 10 in a substantially assembled condition. FIG. 7 shows cover 120, for shielding and preventing contamination of e.g. staple holder 20 and vacuum support 80 during insertion into the patient, and maintaining these and other elements in a sterile environment. Cover 120 also acts as a safety cover during insertion, to prevent injury to the patient due to staple 60 or other portions of device 10. Cover 120 is simply removed from the remainder of device 10, putting device 10 in a "ready" condition, by pulling it off over the mechanisms, etc. at the lower end of device 10.

FIG. 8 is substantially similar to FIG. 7 but eliminates cover 120 and shows additional features in the ready condition. Attached to and extending into staple holder 20 is pressure port 130, for a purpose to be described. Further, endoscope port 140 extends into staple holder 20 for accommodating an endoscope to view the interior of the urethra or bladder. Staple holder 20 is positioned substantially concentrically within vacuum support 80. Staple holder 20 includes retainer mechanism 141 with outwardly biassed retaining legs 142 having staple-engaging portions 143. After implantation of staple 60 in a manner to be described, retaining legs 142 are urged inwardly, by e.g. an outer tube, a position out of contact with staple 60, such that staple holder 20 and associated elements can be removed.

Figure 9:
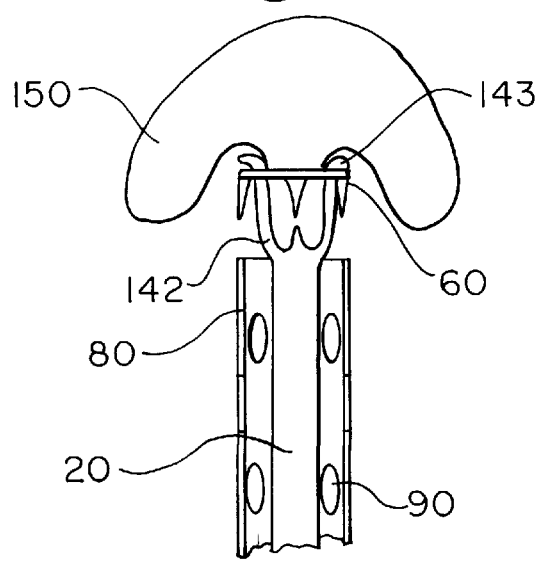
FIG. 9 shows an incontinence treatment device with a deployed balloon, according to an embodiment of the invention.

Balloon or blocking member 150 is housed within staple holder 20 of device 10. Balloon 150 is operably connected to pressure port 130, and according to one example is one-piece with it. As balloon 150 is inflated via pressure port 130, balloon 150 moves from its housed position to the deployed position shown in FIG. 9. Flexible guide 153, made of e.g. plastic, folds out during balloon deployment and substantially prevents balloon 150 from going under staple 60.

As best shown in FIG. 10, balloon 150 also can be in a one-piece configuration with endoscope port 140. Balloon 150 is substantially transparent, according to this embodiment. Endoscope 155 is inserted through port 140 for viewing e.g. the bladder through balloon 150. Direct visualization can help the surgeon ensure proper positioning and engagement of balloon 150 with the bladder walls, as described below.

A method of use according to one embodiment of the invention will now be described, beginning with FIGS. 11–12. First, device 10 is inserted into urethra 160 of the patient to bladder 170. When fully inserted, as shown in FIG. 11, staple holder 40 and staple 60 have passed substantially all the way through bladder neck 175, as shown. The other end of device 10 extends substantially beyond urethral opening 180 for manipulation by the surgeon, as do vacuum port 110, pressure port 130, endoscope port 140, and the screw or other actuation mechanism for retractable wings 50.

Once inserted, pressure is applied through pressure port 130 to inflate balloon 150, causing it to extend from its housed position to the deployed position shown in e.g. FIG. 11. Balloon 150 is ultimately used to create a seal between bladder 170 and urethra 160, substantially preventing urine from passing out of bladder 170.

Once balloon 150 is inflated, a vacuum is pulled through vacuum port 110 and apertures 90 of vacuum support 80. The created vacuum condition in urethra 160 pulls balloon 150 toward urethra 160 to effect the above-described seal and pulls the sides of urethra 160 into a substantially tight relationship against vacuum support 80. According to one embodiment, apertures 90 of vacuum support 80 are large enough to sustain a vacuum in urethra 160, but small enough that significant portions of the walls of urethra 160 are not drawn into support 80. Endoscope 145 can be used to ensure that a proper seal has occurred between the balloon and the walls of bladder 170.

According to an alternative embodiment, balloon 150 and its associated apparatus is not used. Bladder 170 is allowed to collapse during application of the vacuum; the effect of the vacuum on the bladder neck and/or urethra is similar to that which occurs when balloon 170 is used.

Drawing the vacuum through support 80 causes bladder neck 175 and the immediately adjacent portion of urethra 160 to assume a shape akin to the substantially normal anatomical shape shown in FIG. 1. To aid this process, the anterior wall of the vagina can be lifted, e.g. manually or with a trans-vaginal balloon, while the vacuum is applied. These maneuvers elevate urethra 160 and help narrow the urethral neck/bladder neck region 175. Once neck region 175 has assumed a desired shape, staple 60 is implanted in the neck region to maintain that shape, as described below. Of course, device 10 can be constructed to cause neck region 175 to assume any of a number of desired shapes, depending on e.g. the size of the patient, the surgical procedure or surgical environment, etc. For example, the size of the desired shape, the depth thereof, and other characteristics of the shape can be manipulated according to e.g. the surgeon's preference.

Device 10 is positioned such that needles 70 of staple 60 are adjacent neck region 175. To implant the staple, the surgeon then pulls handle 35 such that staple 60 moves towards the urethral opening. Traction on handle 35 pulls staple 60 into the interior tissue of neck 175, below the first layer of tissue, to hold neck 175 in the substantially normal shape caused by the vacuum.

Then, wings 50 are retracted inwardly and disengage and release staple 60. The vacuum applied through port 110 is released, and balloon 150 is deflated. Device 10 then is withdrawn from the urethra. Staple 60 is left behind to form a permanent, implanted support for neck 175.

Ultimately, as shown in FIG. 12, tissue 190 heals over and covers staple 60, making it "invisible" to interior regions of the bladder and urethra. These regions thus are free of foreign bodies, substantially reducing the likelihood of stones or lesions. Additionally, implantation of staple 60 in the manner described occurs substantially without killing the muscle, tissue or nerves of the urethra, all of which are important to normal urinary tract function.

According to preferred embodiments, annulus 65 of staple 60 is of low profile and forms a substantially complete circle. Staple 60 can also be elliptically shaped or formed in a partial-ring or arc shape. Staple 60 can include different numbers of needles 70, and these needles and/or staple 60 itself can be of various diameters, widths and thicknesses. The structural characteristics of staple 60 can be selected based on e.g. the anatomy of the patient, the anatomical location where the staple is placed, the degree of support desired, etc. According to preferred embodiments, staple 60 is comprised of inert metal, plastic or other biocompatible material suitable for implantation in the body and non-corrosive in urine and other fluids. It may also be elastic, to a degree, to allow for some expansion of the neck region 175 while still maintaining structural stability and support. Needles 70 can be formed of a memory metal to form a curve within the penetrated tissue, and to reduce the likelihood that staple 60 will work itself out over time.

Balloon 150 preferably is formed of an elastic, biocompatible material capable of sustaining relatively high pressures. Balloon 150 may be reinforced with internal or external ribbing to provide increased strength and/or support. Balloon 150 can include two dissimilar materials to aid in sealing the junction between bladder 170 and urethra 160. For example, balloon 150 can have a thicker top portion and a thinner bottom portion. As pressure within balloon 150 increases, the thinner bottom portion expands to a greater extent than the thicker top portion, aiding the sealing process. Similarly, the top portion of balloon 150 can have additional rib portions relative to the bottom portion to provide greater structural stability and again to encourage the bottom portion to seal off the bladder at the urethral opening.

A more detailed view of the distal end of device 10, with notations indicating applicable process steps, is shown in FIG. 13.

FIGS. 14-21 illustrate other staple embodiments and associated insertion devices according to embodiments of the invention. In FIG. 14, insertion device 200 includes vacuum port 205 for drawing a vacuum through interior vacuum chamber 210. Balloon 250, extending substantially down the center of device 200, is substantially similar to that described with respect to previous embodiments. Staple 260 preferably is of a different construction, however, and includes one or more base portions 261, needles 263, and one or more receiving portions 265. Note especially FIG. 15, showing a cross-section of staple 260 alone.

Inflating and deploying balloon 250 in the manner of previous embodiments, and then drawing a vacuum through vacuum chamber 210, causes portion 267 of the urethral wall, e.g. in the bladder neck region, to be drawn into the recess defined between base portion 261 and receiving portion 265. In this configuration, the bladder neck and surrounding area are restored to a substantially normal anatomical configuration, or at least to a configuration sufficient to prevent leakage when intra-abdominal pressure pulses occur.

Once the desired, vacuum-induced anatomical configuration is achieved, the surgeon applies pressure to handle 270 in the direction of arrow 280, causing push rod 285 to contact base portion 261 and urge needles 263 through tissue portion 267 and into receiving portion 265. Vacuum seal 287 is provided between push rod 285 and base portion 261. Back pressure against receiving portion 265 can be provided by a ledge or other member fixedly attached to structure surrounding balloon 250 (in its withdrawn position), in a manner akin to portions 143 in FIGS. 8-9 and 13.

A variety of structural features are contemplated to keep needles 263 retained within receiving member 265. Receiving member 265 can cause needles 263 to curve as they enter and penetrate, e.g. by including one or more internal, curved, substantially impenetrable portions. Needles 263 curve along the substantially impenetrable material as they enter, much in the manner of a conventional paper stapler. Alternatively, or additionally, needles 263 can be formed of a memory-type metal, the memory causing the needles to curve so as to prevent removal from receiving member 265.

Once needles 263 have been secured in receiving member 265, the vacuum is released, balloon 250 is deflated, and device 200 is withdrawn from the urethra. Staple 260 remains, holding the bladder neck (or other anatomical region) in the desired configuration. Other features of these embodiments are substantially as shown and described with respect to previous embodiments. For example, staple 260 can be ring-shaped, elliptical, arc-shaped, of different dimensions, etc.

Figure 16:
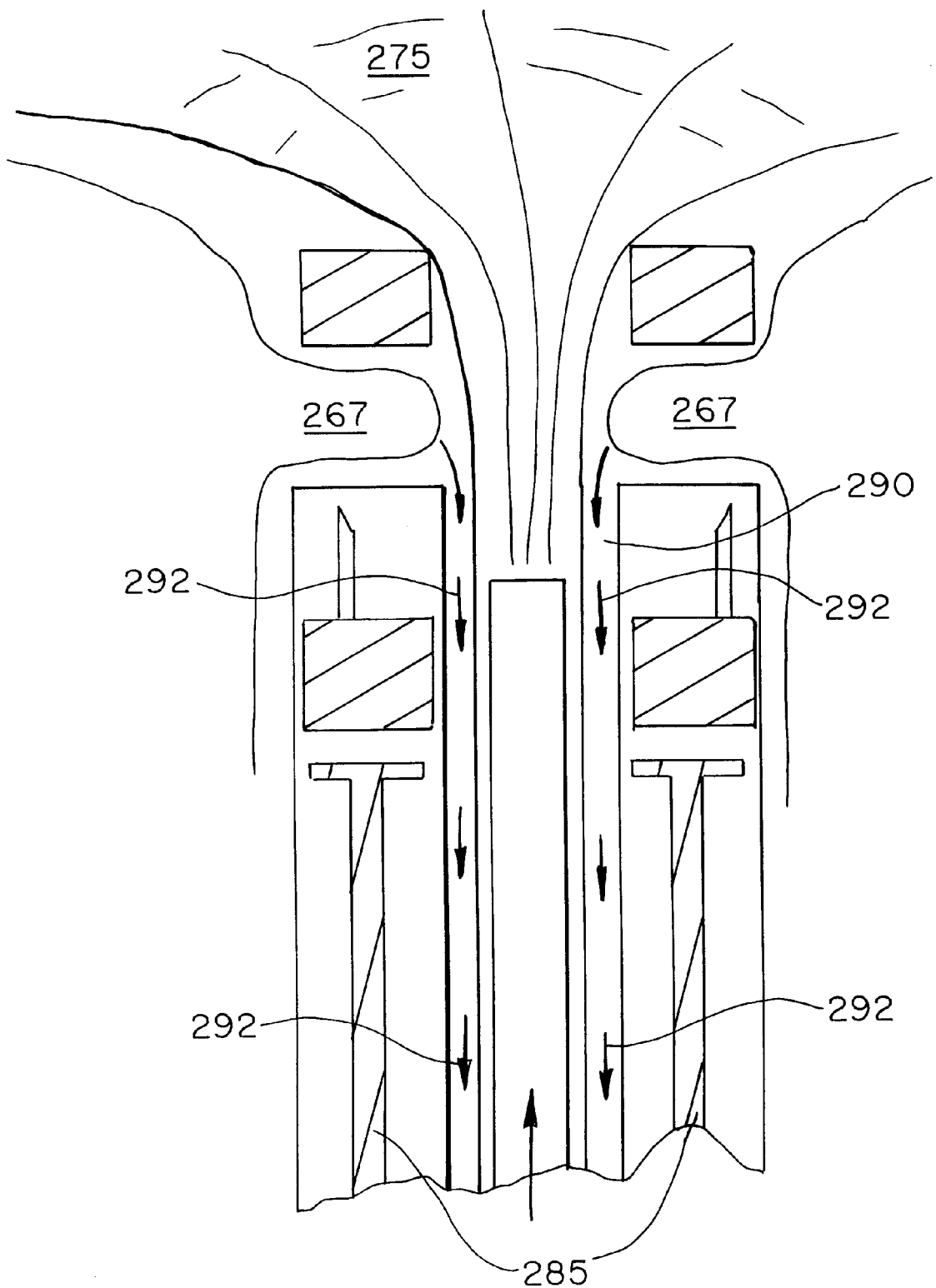
FIG. 16 shows an incontinence treatment device with indrawn tissue, according to an embodiment of the invention.
Figure 17:
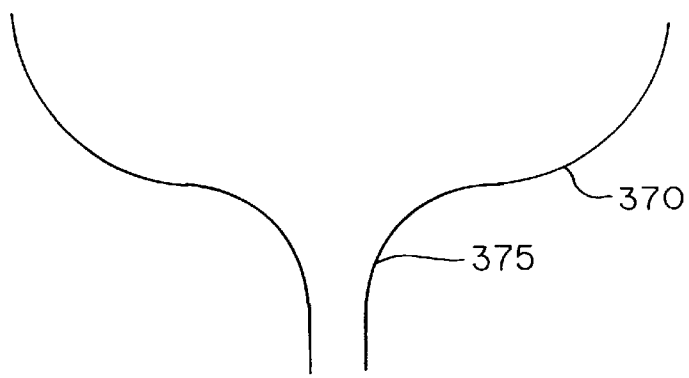
FIGS. 17–20 show an incontinence treatment device as it is inserted into a sagging bladder/urethra, according to embodiments of the invention.
Figure 18:
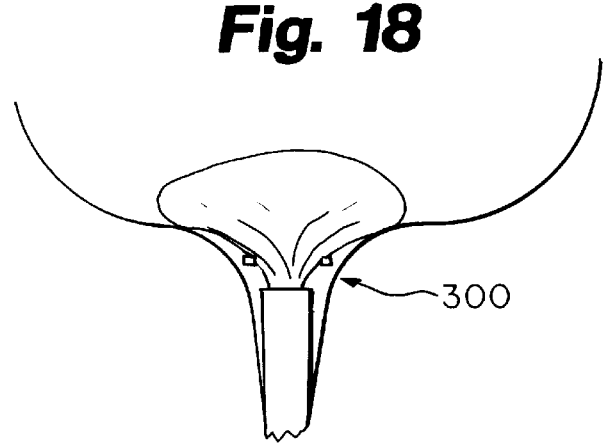
Figure 19:
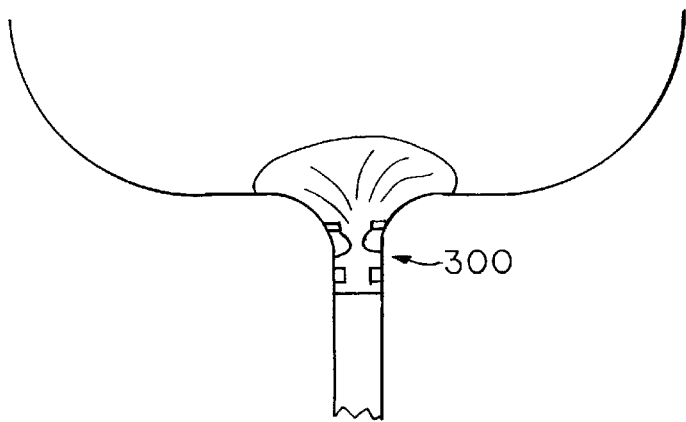
Figure 20:
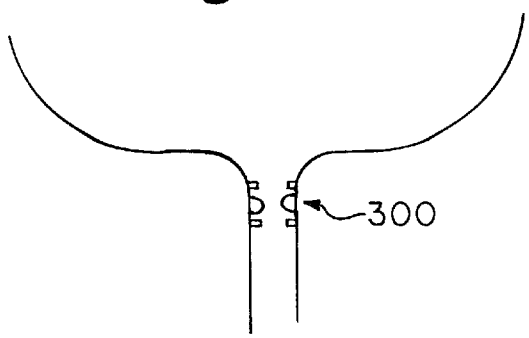

The FIG. 16 embodiment is somewhat similar to the embodiment of FIG. 14, but a preferably lightweight, strong retractable plastic portion 275 in the form of an inverted umbrella is used to provide the vacuum seal between the bladder and the urethra. Also shown in FIG. 16 is a central open lumen 290 for an endoscope to be inserted through the center of the device, for visually confirming that the plastic portion is positioned properly to form the desired seal. Lumen 290 is for pulling a vacuum in the direction of arrows 292, in the manner described earlier. Tissue and muscle 267 are drawn inwardly by the vacuum, as shown.

FIGS. 17-20 generally show the anatomical correction achievable according to embodiments of the invention. As shown, sagging bladder 370 and neck region 375 of FIG. 17 receive insertion device 300 in FIG. 18. Vacuum is applied and a more normal anatomical configuration is induced in FIG. 19, as described previously. Finally, the staple is closed, as in FIG. 20, to maintain the desired anatomical configuration achieved by vacuum.

FIG. 21 shows an additional staple embodiment. Staple 360 includes needles 363, of greater relative length than the needles of previous embodiments, for penetration through a relatively large tissue region 367 between annular staple supports 361, 365. This arrangement supports a greater length of the urethra while still allowing the sphincter to act naturally, as with previous embodiments. Other features of this embodiment are substantially as described with previous embodiments.

FIGS. 22-28 show cross-sections of a preferred embodiment of the invention that uses many of the apparatus and method principles described above. FIG. 22 is a cross-sectional view of device 400 in a substantially assembled condition, and FIGS. 23–28 show and highlight individual components of device 400.

Device 400 implants a two-part stapling mechanism comprising locking member or staple ring 410 and staple 420, shown in e.g. FIG. 23. Depending needles 423 of staple 420 each preferably include a tapered-surface tip or barb 425 for engaging behind and clipping over staple ring 410. According to one embodiment, needles 423 are substantially flexible with respect to the base portion of staple 420 and snap into locking engagement with staple ring 410. This structure provides firm securement of the staple in the bladder neck. Further, device 400 causes staple 420 to slide along an inner supporting tube, as will be described, for better control and to avoid "rocking," i.e. insertion at an undesirable angle. Before implantation, staple ring 410 rests on bead 428.

FIG. 24 shows staple insertion/actuator mechanism 430, to which handle 435 (FIG. 22) is attached at its proximal end. Mechanism 430 includes leg member 440 and pedestal portion 445, on which staple 420 rests. When the surgeon or other medical professional moves handle 435 farther into the urethra, leg member 440 and pedestal 445 push staple 420 along an inner supporting tube towards staple ring 410. Eventually, barbs 425 pierce the pulled-in tissue, as described with respect to previous embodiments, and snap behind staple ring 410 for a secure engagement.

FIG. 25 illustrates staple ring retainer/release mechanism 450, attached to handle 455 (FIG. 22) at its proximal end. Mechanism 450 includes outwardly biased retaining legs 460 with staple-ring engaging tips 470. Tips 470 include ramped portions 473, which extend outwardly through slots or other track structure in a surrounding tube, described with respect to e.g. FIG. 26, below. Once the stapling device is implanted, the medical professional urges release mechanism 450 farther into the urethra. This causes ramped portions 473 of tips 470 to ride within the tracks in the outer tube, which in turn urges retaining legs 460 inwardly. Once tips 470 are urged inwardly far enough to clear staple ring 410, and the balloon is deflated, the entire mechanism 450 can be withdrawn from the urethra through the center of staple ring 410.

FIG. 26 illustrates mounting device 480, secured at its proximal end to device support 485 (FIG. 22). Mounting device 480 includes tube 490 with recessed portion 495 for accommodating the pulled-in tissue. Device 480 also includes a distal wall portion with slots or tracks 475, through which ramped portions 473 of tips 470 protrude.

FIG. 27 shows vacuum retainer mechanism 500, which defines vacuum apertures 510 for drawing a vacuum through vacuum port 515 (FIG. 22), substantially in the manner described earlier.

Finally, FIG. 28 shows balloon and catheter assembly 520. Catheter 530 preferably extends down the center of device 400, and is coupled with endoscope port 535 (FIG. 22) to accommodate an endoscope, as described earlier. Balloon 540 is illustrated in its undeployed position, and is coupled with pressure port 550 for inflation and deployment, in a manner substantially as described previously.

Device 400 optionally can be fit into a handle mechanism made of plastic or other suitable material. The handle preferably has slots to accommodate e.g. handle 435 of insertion/actuator mechanism 430, handle 455 of staple ring retainer mechanism 450, device support 550, etc. The handle can be disposable or constructed for reuse, as desired.

FIGS. 29–41 show handles and associated structure according to additional embodiments of the invention, incorporating many of the previously described features in a more refined form. Many of the concepts embodied in FIGS. 29–41 have already been described; to simplify the disclosure, many such concepts will not be repeated. For example, the various balloon/inflatable members described above will not be described again here.

As shown in FIGS. 29–30, the illustrated incontinence treatment device 600 includes base handle 605, which preferably is one-piece with or otherwise attached to substantially cylindrical, upwardly extending member 610. Member 610, in turn, preferably is one-piece with or otherwise attached to ring retainer 620. Ring retainer 620 defines recessed portion 630, for accommodating tissue and/or muscle pulled therein by a vacuum source in a manner described previously. Further details of retainer 620 are provided below.

FIGS. 29–30 also illustrate staple-release handle 650, disposed above base handle 605 in this embodiment. Staple-release handle 650 preferably is one-piece with or attached to substantially cylindrical, upwardly extending member 660 (not visible in FIGS. 29–30, but shown in e.g. FIGS. 36–37), which preferably surrounds member 610. Disposed above staple-release handle 650 is staple-advance handle 670, which is one-piece with or rigidly attached to substantially cylindrical, upwardly extending member 680. Member 680 preferably surrounds member 660. Finally, FIG. 29 illustrates base or support 485, which is one-piece with or rigidly attached to vacuum retainer mechanism 500. Mechanism 500 includes vacuum apertures 510 and has already been described.

Figure 31:
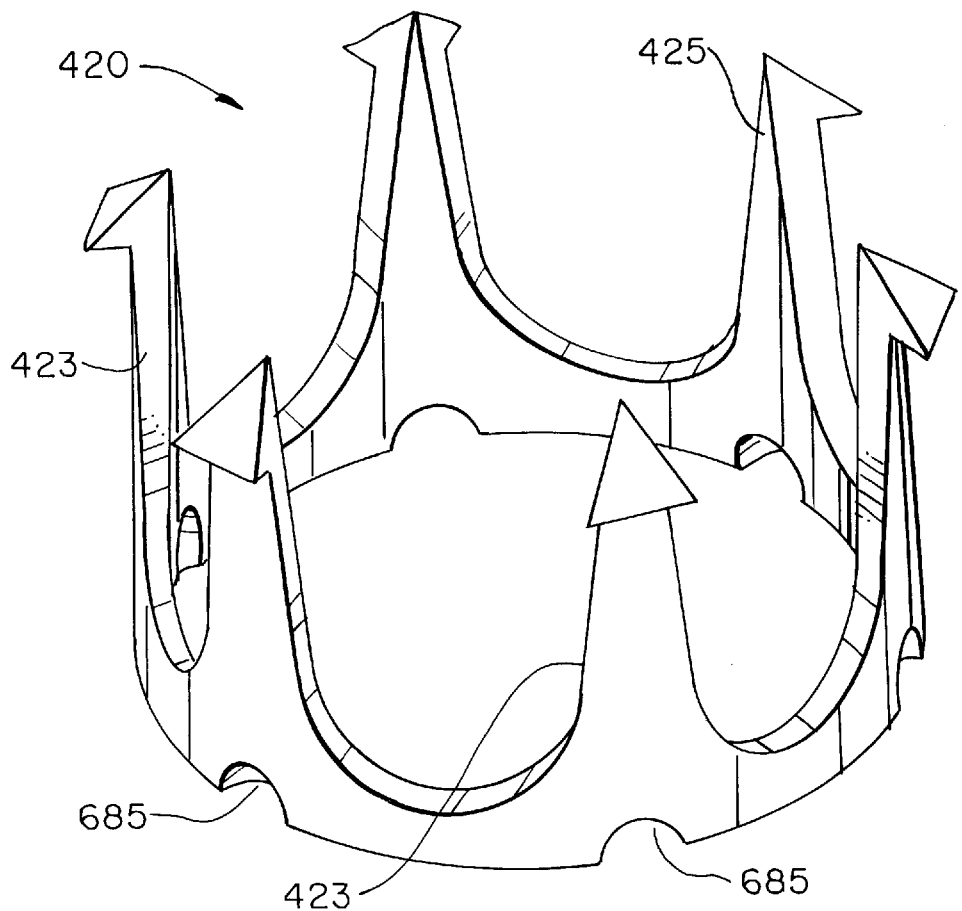
FIG. 31 is a perspective view of a staple, according to an embodiment of the invention.
Figure 31A:
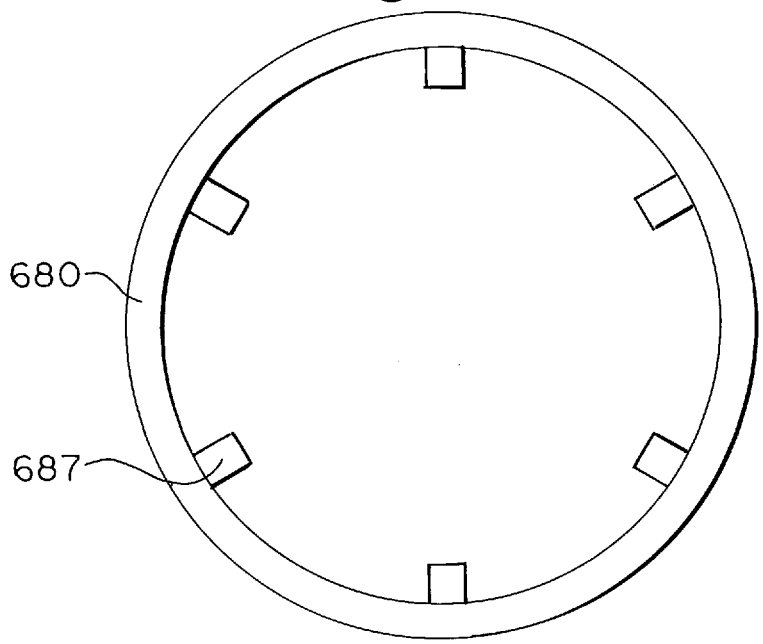
FIG. 31A is a top view of a support for the staple of FIG. 31.

FIG. 31 illustrates staple 420, which has been described previously. Also visible in FIG. 31 are detents 685. According to one embodiment, shown in FIG. 31A, upwardly extending member 680 includes a plurality of radially inwardly extending pins 687. Pins 687 fit within detents 685 of staple 420, to provide support for staple 420 relative to member 680. Detents 685 also allow rotational indexing, so that staple 420 can be prealigned before a treatment procedure begins. Member 680 can be rotated, e.g. via handle 670 or otherwise, until needles 423 are properly aligned with respect to ring retainer 620, which will now be described in more detail.

As shown in FIG. 32, ring retainer 620 includes a plurality of sprung legs 690. The illustrated embodiment includes six such legs 690, but of course a greater or lesser number of legs, for example three legs, is also contemplated. Providing fewer legs tends to allow more room for the balloon or other structure disposed within device 600. Each leg 690 includes preferably includes one or more slanted surfaces 700, 720. Such surfaces preferably engage structure external to mechanism 620, to drive legs 690 inwardly after staple 420 has been brought through the tissue/muscle in gap 630 and into contact with staple ring 410. This contact occurs as the medical professional moves staple-release handle 650. Moving legs 690 inwardly withdraws legs 690 from staple ring 410 and removes legs 690 from supporting contact with staple ring 410 at groove 710, once it is desired to withdraw treatment device 600 from the bladder/urethra.

As best shown in FIG. 37, ring retainer 620 also defines recesses 730 at the uppermost portion of upwardly extending member, for accommodating depending needles 423 of staple 420. Recesses 730 preferably are disposed directly beneath gaps 740 between legs 690 of retainer 620, such that needles 423 slide from recesses 730, across gap 630 and into gaps 740. This configuration assures accurate and even positioning of needles 423 behind staple ring 410. As referenced previously, handle 670 can be turned to rotationally index staple 420 for correct positioning.

Figure 33:
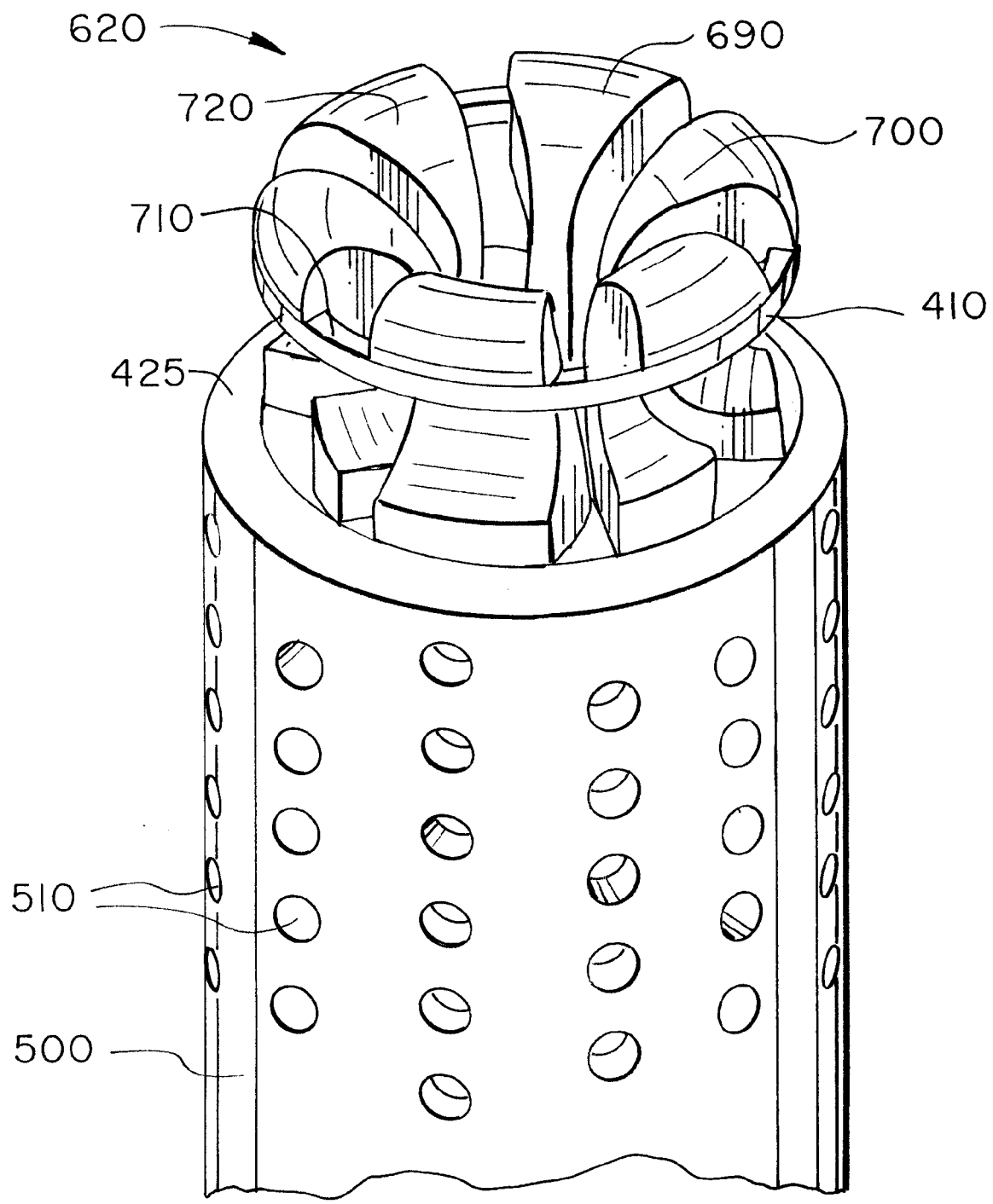
FIG. 33 is a perspective view of the FIG. 32 device.

In use, ring retainer 620 is first disposed as shown in FIG. 32–33. The staple is mounted on pins 687 and rotationally aligned with respect to retainer 620. The device is inserted into the patient in the manner described previously. Vacuum is applied and the tissue/muscle is drawn into gap 630, also as described previously. Staple 420 then is urged across gap 630, by movement of staple-advance handle 670, through the tissue and into contact with staple ring 410. As shown, barbs 425 each include a tapered surface for engaging and sliding relative to ring 410, and depending needles 423 of staple 420 then lock into place behind ring 410. The configuration of FIGS. 34–35 thus is achieved.

Figure 34:
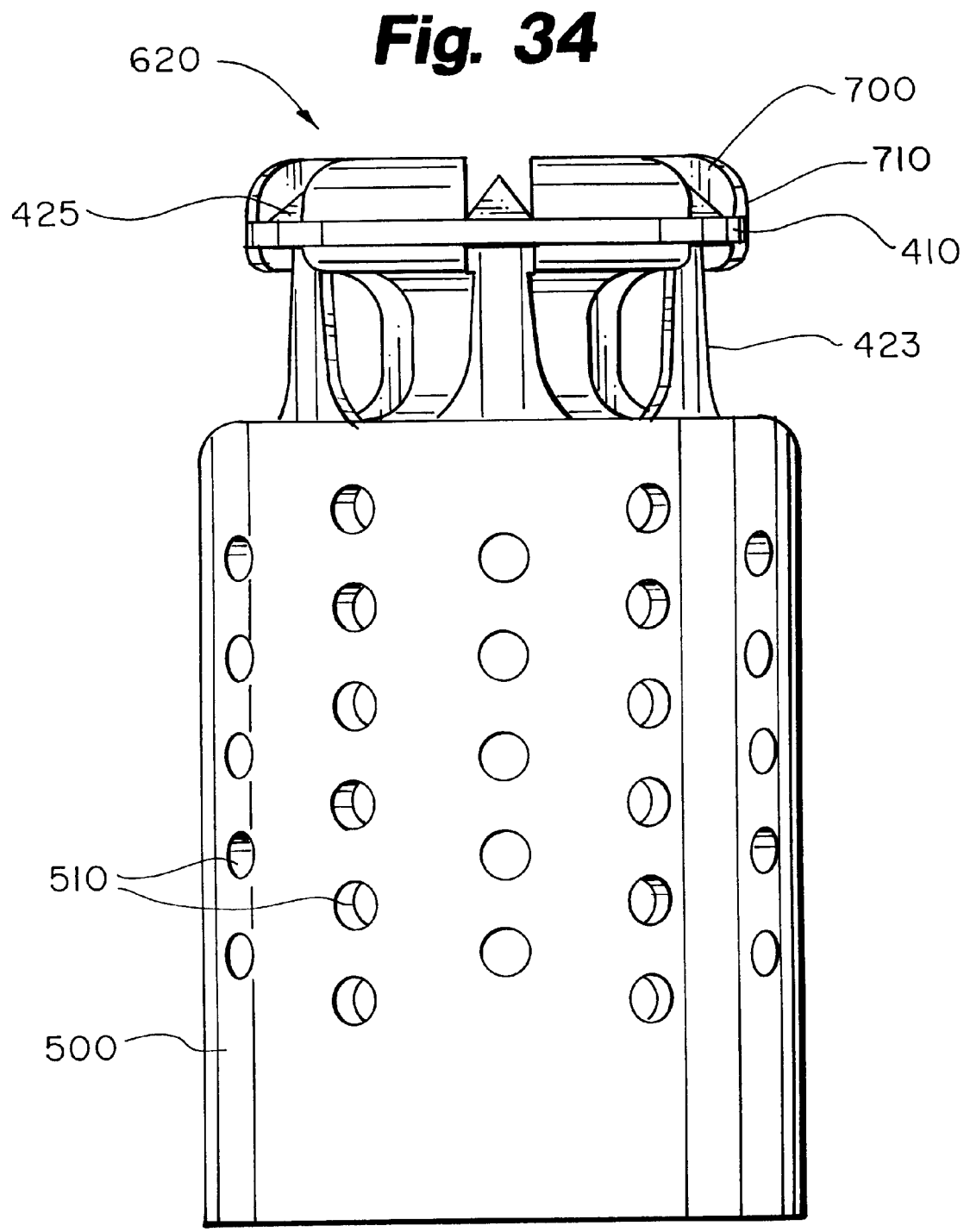
FIG. 34 is a side view similar to FIG. 32, but with portions of the staple disposed behind the staple ring, according to an embodiment of the invention.
Figure 35:
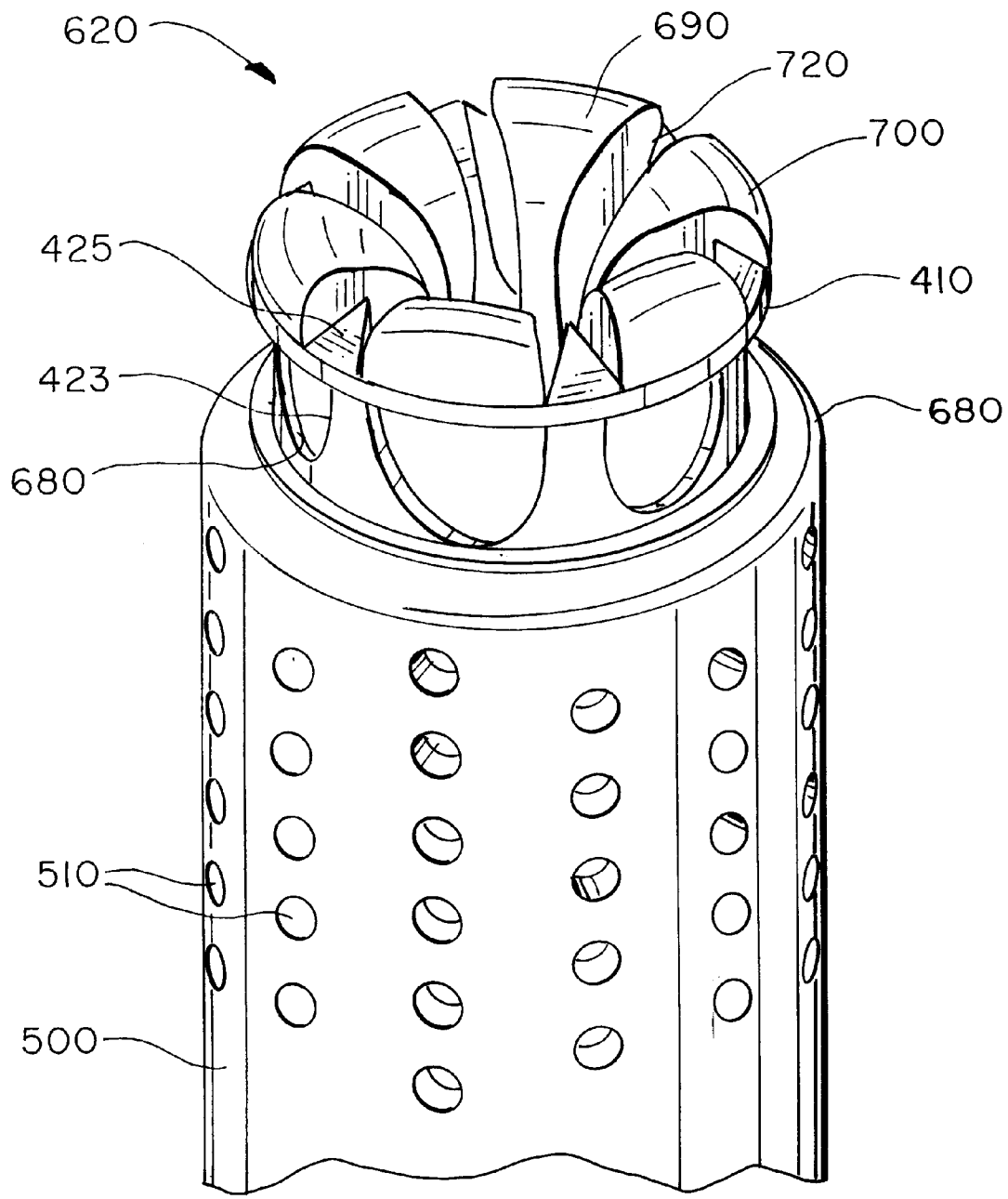
FIG. 35 is a perspective view of the FIG. 34 device.

As is clear from the figures, e.g. FIGS. 33–35, needles 423 can lock into place with respect to ring 410 at any angle or orientation of ring 410, about e.g. the central axis of ring 410. In the illustrated example, that central axis is also the longitudinal axis of the overall device. As is also clear from the figures, needles 423, at ring 410, are open to the central axis of ring 410 when needles 423 are in locking engagement with ring 410.

Figure 38:
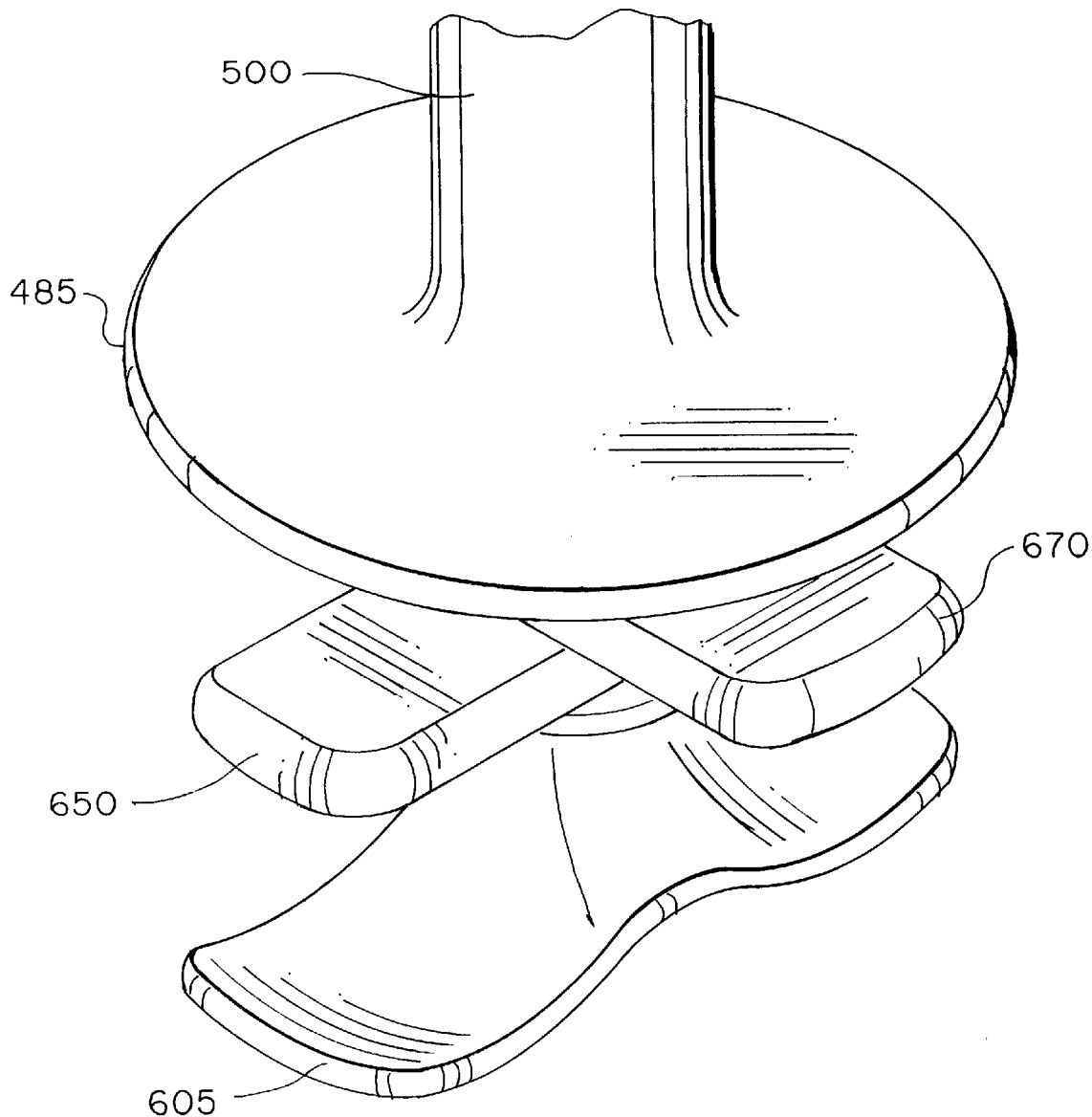
FIGS. 38–41 are lower perspective views of incontinence treatment devices, according to alternative embodiments of the invention.
Figure 39:
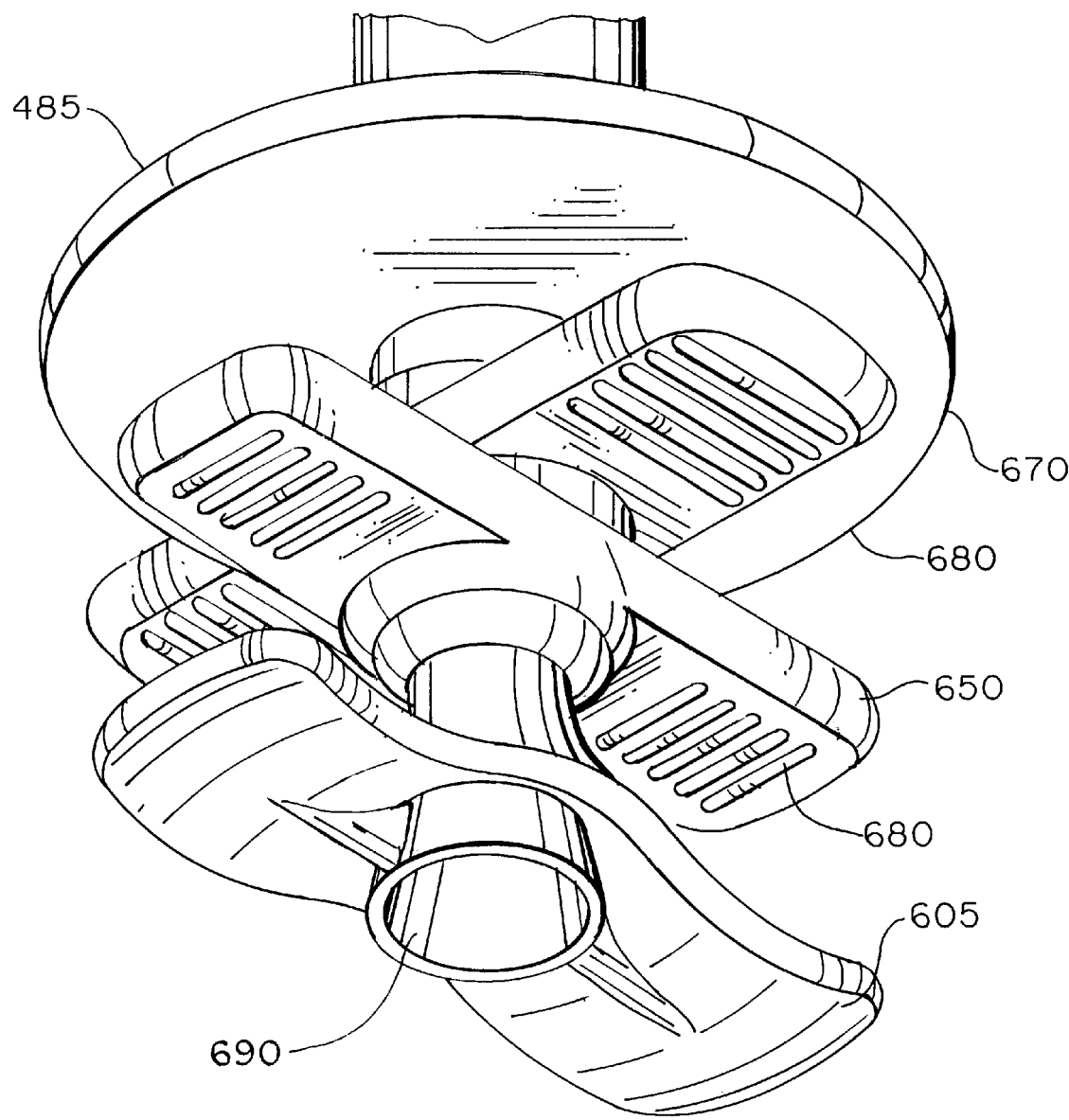

FIG. 38 shows a streamlined version of the lower end of device 600. FIG. 39 shows the undersides of handles 605, 650 and 670. Ridges 680 provide a better gripping surface for the surgeon or other medical professional. FIG. 39 also illustrates aperture 690, through which extend e.g. the catheter and endoscope described previously, along with other instruments that might be desirable for a particular procedure, such as a camera, electrocautery, endoscopic suture device, etc.

Figure 40:
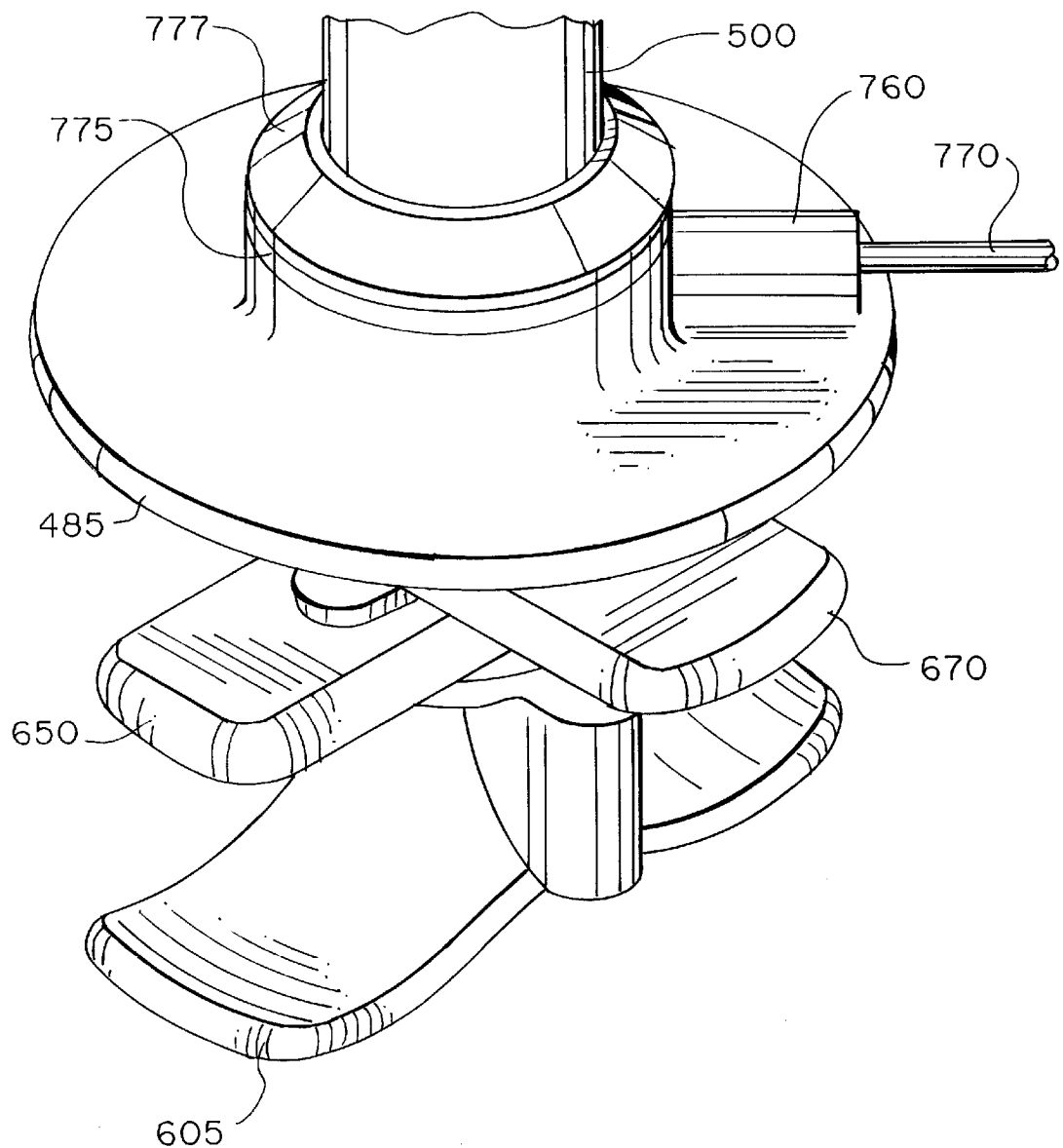
Figure 41:
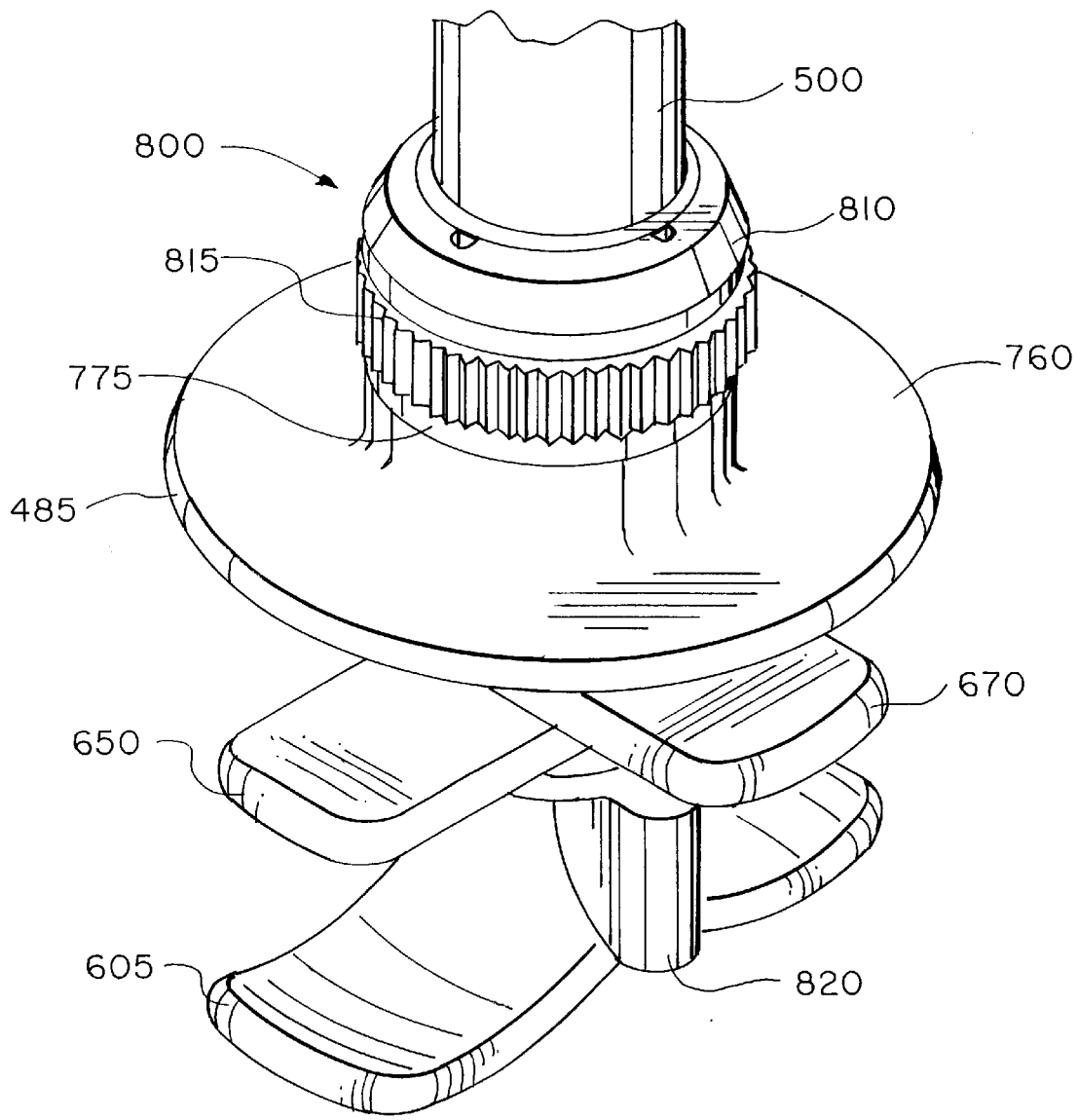
Figure 42:
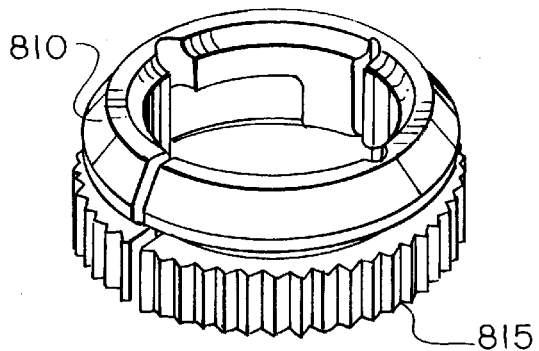
FIG. 42 is a top perspective view of a thumbwheel mechanism, according to an embodiment of the invention.
Figure 43:
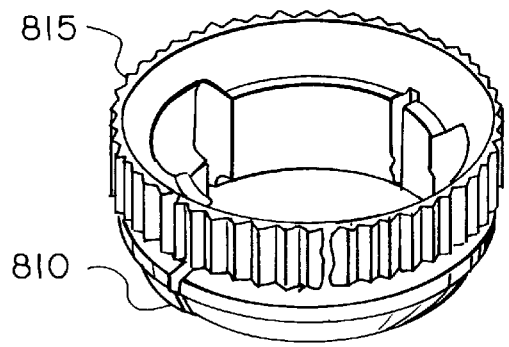
FIG. 43 is a bottom perspective view of the FIG. 42 thumbwheel.
Figure 44:
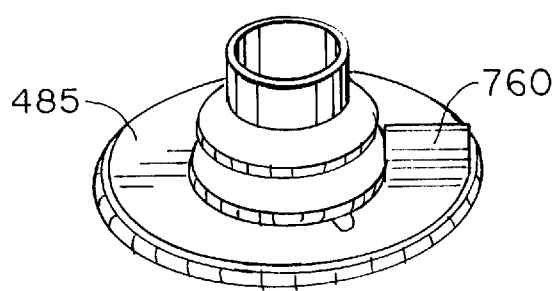
FIG. 44 is a top perspective view of a handle outer shell, according to an embodiment of the invention.
Figure 45:
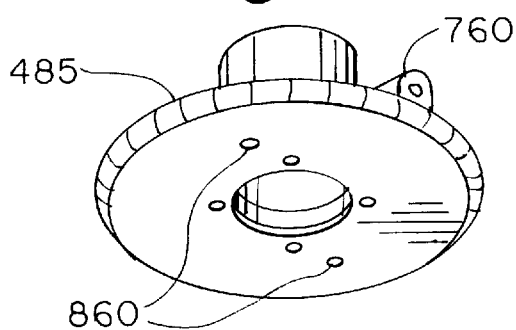
FIG. 45 is a top view of the FIG. 44 shell.
Figure 46:
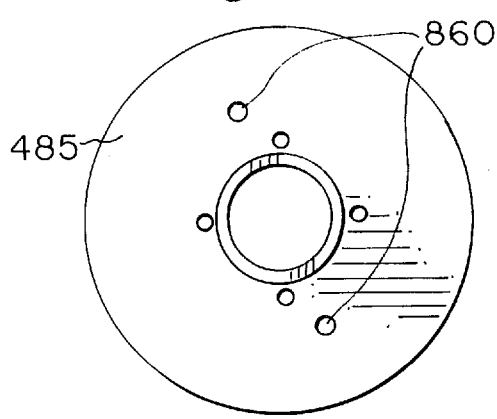
FIG. 46 is a bottom perspective view of the FIG. 44 shell.
Figure 47:
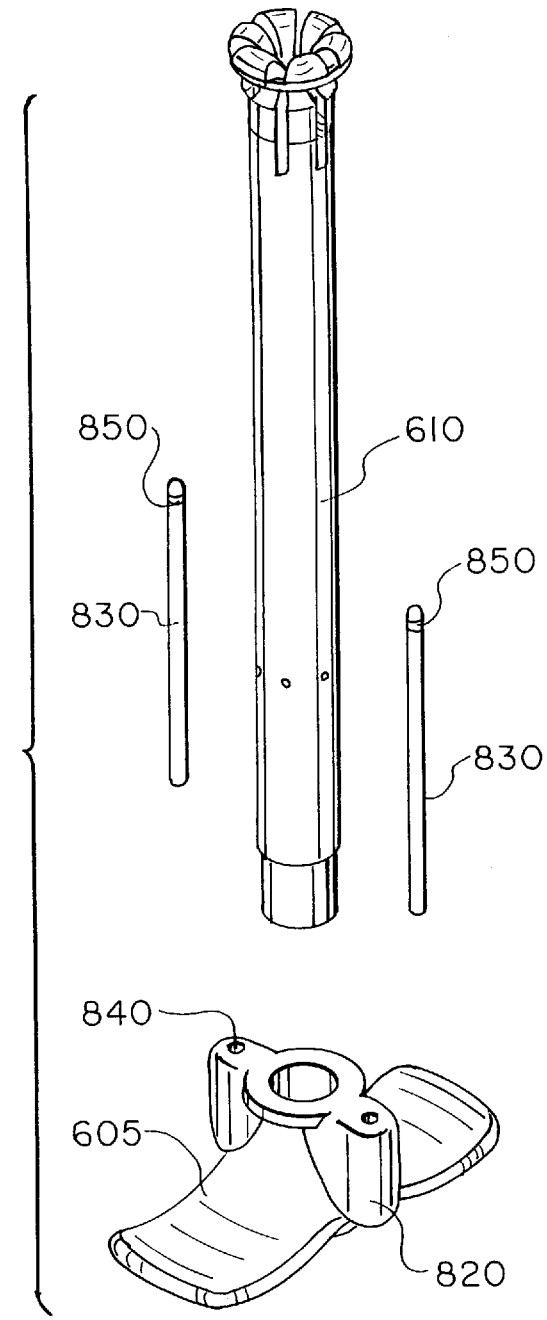
FIG. 47 is an exploded view showing a ring retainer assembly according to an embodiment of the invention.

Turning to FIG. 40, the lower end of device 600 includes vacuum port 760 with associated vacuum line 770, as shown. Vacuum port 760 preferably is one-piece with and molded as a part of base 485. Sealing ring 775 provides a vacuum seal between the upper portion 777 of the hub of base 485, and the remainder of base 485.

Locking mechanism 800 will now be described with reference to FIGS. 41–47. Locking mechanism 800 includes thumbwheel 810 with ridged surface 815, rod support 820, and upwardly extending locking rods 830, shown in FIG. 47. Locking rods 830 extend upwardly from apertures 840 in supports 820, and into and through corresponding apertures in handle 670. Rods 830 include detents 850 at their upper ends, for engaging and locking into apertures 860 (FIGS. 45–46) in base 485. Locking rods 830 extend on opposite sides of handle 650. Thus, handles 605, 650 and 670, as well as base 485, are all held in a substantially fixed angular orientation with respect to each other. Handles 650, 670 preferably are allowed to slide along locking rods 830. Thumbwheel 810 is placed over and tightened down with respect to base 485, holding all of the component parts substantially in place with respect to each other.

With all of the embodiments, the urethra and bladder neck region are supported in a substantially normal anatomic configuration, allowing the sphincter to act normally without the downward and radial forces of the bladder fluid on it. Permanent correction of e.g. USI is achieved, using minimally invasive techniques and with minimal or no necrosis of the tissue.

While the invention has been described with respect to particular embodiments, the description herein is intended to be illustrative and not limiting. For example, although specific reference has been made to the urethra and bladder, embodiments of the invention can be used to repair or sustain other anatomical structures, such as the rectum, anal canal, liver or other organs. Embodiments for use in male patients can be of greater length than those for use in female patients; dimensions can generally be chosen in accordance with particular anatomies. Further, the procedures described herein can be performed without creating a vacuum, wherein the restoration of the urethra/bladder neck is accomplished with physical maneuvering. As will be apparent to those of ordinary skill, the structures and other concepts disclosed with respect to one embodiment or figure can be applied, and in many cases are intended to be applied, in combination with those of other embodiments or figures. Various other modifications and changes will be apparent to those of ordinary skill.

What is claimed is:

1. A surgical staple device, comprising:

a substantially ring-shaped hollow base portion;

a plurality of needle members upstanding from the base portion; and a substantially ring-shaped locking member for receiving the needle members, the locking member initially being separated from the base portion and needle members, the locking member having an inside portion and an outside portion, the inside portion of the locking member being constructed to receive the needle members and the needle members being constructed to enter into locking engagement with respect to the locking member;

wherein the surgical staple device is constructed of a biocompatible material;

further wherein the locking member is constructed such that the needle members can enter into said locking engagement with respect to the locking member at any angular orientation of the locking member about its central axis.

2. The surgical staple device of claim 1, wherein the needle members are substantially flexible with respect to the base portion, the needle members snapping into locking engagement with the locking member.

3. The surgical staple device of claim 1, wherein the needle members each include a tapered upper surface for engaging the inner surface of the locking member and for sliding with respect to the inner surface of the locking member as the needle members are advanced into the locking member.

4. The surgical staple device of claim 3, wherein the needle members each snap into place with respect to the locking member, once the tapered upper surface clears the inside portion of the locking member.

5. The surgical staple device of claim 1, wherein the base portion defines a plurality of detents for supporting the base portion with respect to a staple insertion mechanism.

6. The surgical staple device of claim 5, wherein the detents are disposed directly underneath the upstanding needle members on a side of the base portion opposite the needle members.

7. The surgical staple device of claim 1, wherein the base portion is substantially circular.

8. A surgical treatment device, comprising:

a surgical staple, the surgical staple comprising a substantially ring-shaped hollow base portion, a plurality of needle members upstanding from the base portion, and a substantially ring-shaped locking member for receiving the needle members, the locking member initially being separated from the base portion and needle members, the locking member having an inside portion and an outside portion, the inside portion of the locking member being constructed to receive the needle members and the needle members being constructed to enter into locking engagement with respect to the locking member, wherein the surgical staple device is constructed of a biocompatible material;

delivery structure for supporting the surgical staple and delivering the surgical staple to a desired anatomical site of a patient;

movement apparatus, operatively coupled with the delivery structure, for moving anatomical tissue into position between the needle members and the locking member; and a staple advancing mechanism for advancing the needle members through the anatomical tissue and into locking engagement with the locking member, the surgical staple thus holding the anatomical tissue in a desired configuration.

9. The surgical treatment device of claim 8, wherein the movement apparatus comprises a vacuum device for drawing desired tissue into a new anatomical position.

10. The surgical treatment device of claim 9, wherein the movement apparatus further comprises a blocking device, operatively coupled with the vacuum device, for preventing the vacuum device from applying vacuum to a portion of the anatomy of the patient.

11. The surgical treatment device of claim 10, wherein the blocking device comprises an inflatable mechanism.

12. The surgical treatment device of claim 8, wherein the movement apparatus is physically connected to the delivery structure.

13. The surgical treatment device of claim 8, being constructed for use in minimally invasive surgical procedures.

14. A surgical treatment device, comprising:

delivery structure for supporting a surgical staple and delivering the surgical staple to a desired anatomical site of a patient;

movement apparatus, operatively coupled with the delivery structure, for moving anatomical tissue into position with respect to the surgical staple, the movement apparatus comprising a vacuum device; and a staple advancing mechanism for moving the surgical staple into a holding configuration with respect to the anatomical tissue, the surgical staple thus holding the anatomical tissue in a desired configuration.

15. The surgical treatment device of claim 14, wherein the movement apparatus further comprises a blocking device, operatively coupled with the vacuum device, for preventing the vacuum device from applying vacuum to a portion of the anatomy of the patient.

16. The surgical treatment device of claim 15, wherein the blocking device comprises an inflatable mechanism.

17. The surgical treatment device of claim 15, wherein the blocking device comprises a balloon constructed for insertion into the bladder of the patient, further wherein the anatomical tissue is at least a portion of the bladder neck and/or urethra.

18. The surgical treatment device of claim 14, wherein the delivery structure comprises a staple retaining mechanism, the staple retaining mechanism comprising a plurality of sprung leg members.

19. The surgical treatment device of claim 18, wherein the staple retaining mechanism further comprises a groove for accommodating a locking ring of the surgical staple.

20. The surgical treatment device of claim 18, wherein the sprung leg members define a plurality of gaps therebetween, the gaps accommodating upstanding portions of the surgical staple.

21. The surgical treatment device of claim 14, wherein the delivery structure comprises a plurality of concentrically disposed substantially cylindrical members, one of the substantially cylindrical members being constructed to advance the staple into the holding configuration, and another of the substantially cylindrical members being constructed to release the staple from the delivery structure after the holding configuration has been achieved.

22. The surgical treatment device of claim 14, wherein the delivery structure comprises a plurality of handles for actuation by a user of the device, one of the handles being constructed to advance the staple into the holding configuration, and another of the substantially cylindrical members being constructed to release the staple from the delivery structure after the holding configuration has been achieved.

23. The surgical treatment device of claim 22, wherein the delivery structure further comprises locking structure for substantially fixing the angular position of the handles with respect to each other.

24. The surgical treatment device of claim 23, wherein the locking structure comprises at least one locking rod extending through or alongside the handles.

25. The surgical treatment device of claim 14, being constructed for use in minimally invasive surgical procedures.

26. The surgical treatment device of claim 14, wherein the vacuum device comprises a substantially cylindrical member defining vacuum apertures.

27. The surgical treatment device of claim 26, where the vacuum device is substantially concentrically disposed with respect to the delivery device.

28. A method of treating urinary incontinence in a patient, the method comprising:

inserting a surgical treatment device into at least the urethra of the patient;

applying a vacuum with the surgical treatment device to draw at least a urethra portion and/or bladder neck portion of the patient into a desired configuration;

delivering a surgical staple to the patient with the device, the staple holding the desired configuration;

releasing the staple from the device; and withdrawing the device from the patient.

29. The method of claim 28, further comprising:

inserting a balloon into the bladder of the patient;

inflating the balloon;

blocking application of vacuum to at least the bladder with the balloon;

deflating the balloon; and withdrawing the balloon from the patient.

30. Urinary incontinence treatment apparatus, comprising:

means for applying a vacuum to draw at least a urethra portion and/or bladder neck portion of a patient into a desired configuration;

means for delivering a surgical staple to the patient, the staple holding the desired configuration; and means for releasing the staple so that it remains within the patient.

31. The apparatus of claim 30, further comprising:

means for blocking application of vacuum to at least the bladder; and means for withdrawing the means for blocking from the patient.

32. The apparatus of claim 31, wherein the means for blocking comprises a balloon.

33. The device of claim 1, wherein the needle members, at the locking member, are open to the central axis of the locking member when the needle members are in locking engagement with the locking member.

34. The device of claim 14, wherein the staple, in the holding configuration, comprises a first staple portion locked into place with respect to a second staple portion.

35. The device of claim 14, wherein the holding configuration is a locked configuration.

\* \* \* \* \*